(12) United States Patent
Belushkin et al.

(10) Patent No.: US 12,174,182 B2
(45) Date of Patent: Dec. 24, 2024

(54) PLASMONIC BIOSENSOR

(71) Applicant: ECOLE POLYTECHNIQUE FEDERALE DE LAUSANNE (EPFL), Lausanne (CH)

(72) Inventors: Alexander Belushkin, Lausanne (CH); Filiz Yesilköy, Ecublens (CH); Hatice Yanik Altug, Mex (CH)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 914 days.

(21) Appl. No.: 17/040,692

(22) PCT Filed: Mar. 27, 2019

(86) PCT No.: PCT/IB2019/052475
§ 371 (c)(1),
(2) Date: Sep. 23, 2020

(87) PCT Pub. No.: WO2019/186416
PCT Pub. Date: Oct. 3, 2019

(65) Prior Publication Data
US 2021/0048435 A1  Feb. 18, 2021

Related U.S. Application Data

(60) Provisional application No. 62/648,462, filed on Mar. 27, 2018.

(51) Int. Cl.
*G01N 33/543* (2006.01)
*G01N 21/552* (2014.01)
(Continued)

(52) U.S. Cl.
CPC ..... *G01N 33/54373* (2013.01); *G01N 21/554* (2013.01); *G01N 21/59* (2013.01);
(Continued)

(58) Field of Classification Search
CPC .......... G01N 33/54373; G01N 21/554; G01N 21/59; G01N 33/54346; G01N 33/68; G01N 2021/5903
See application file for complete search history.

(56) References Cited

U.S. PATENT DOCUMENTS

2014/0204372 A1   7/2014 Pang et al.
2014/0206101 A1*  7/2014 Liu ...................... G01N 21/554
                                                          422/69

(Continued)

OTHER PUBLICATIONS

Cetin et al (Handheld high-throughput plasmonic biosensor using computational on-chip imaging, Light: Science & Applications (2014) 3, e122). (Year: 2014).*

(Continued)

*Primary Examiner* — Ann Montgomery
*Assistant Examiner* — Chau N. B. Tran
(74) *Attorney, Agent, or Firm* — Nixon & Vanderhye P.C.

(57) ABSTRACT

The present invention relates to a plasmonic biosensor system. The system includes a nano-hole array device comprising at least one nano-hole array (NHA) including at least one or a plurality of nano holes (NH), an image sensor (A3) for capturing light provided by a light source (A1) and transmitted through the nano-hole array (NHA), and at least one or a plurality of nano-particles (NP) configured to be received by the nano-holes (NH) of the nano-hole array (NHA).

16 Claims, 12 Drawing Sheets

Figure 1:
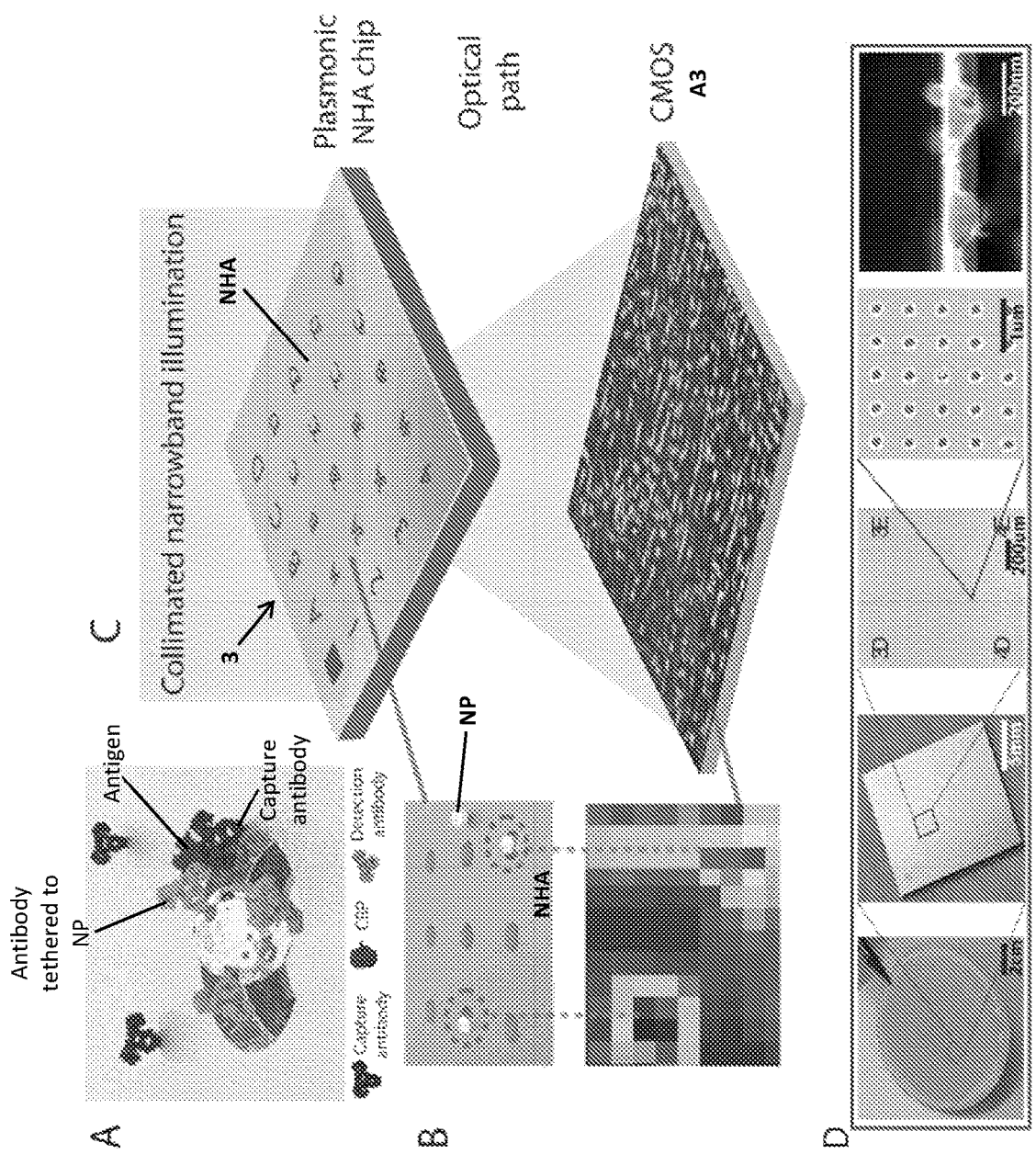

(51) Int. Cl.
  G01N 21/59 (2006.01)
  G01N 33/68 (2006.01)
(52) U.S. Cl.
  CPC ....... *G01N 33/54346* (2013.01); *G01N 33/68* (2013.01); *G01N 2021/5903* (2013.01); *G01N 2201/0221* (2013.01); *G01N 2333/4737* (2013.01); *G01N 2333/76* (2013.01); *G01N 2440/32* (2013.01); *G01N 2800/26* (2013.01); *G01N 2800/52* (2013.01)

(56) References Cited

U.S. PATENT DOCUMENTS

2017/0023476 A1 1/2017 Altug et al.
2017/0284935 A1 10/2017 Ndukaife et al.

OTHER PUBLICATIONS

Chen (Align and Subtract Two Images, 2017) (Year: 2017).*
Cetin et al (Handheld high-throughput plasmonic biosensor using computational on-chip imaging, Light: Science & Applications (2014) 3, e122). Supplement document (Year: 2014).*
International Search Report for PCT/IB2019/052475 mailed Sep. 19, 2019, 5 pages.
Written Opinion of the ISA for PCT/IB2019/052475 mailed Sep. 19, 2019, 10 pages.
Cetin et al., "Handheld high-throughput plasmonic biosensor using computational on-chip imaging", Light: Science & Applications, vol. 3, no. 1, Jan. 3, 2014, 10 pgs.
Sharpe et al., "Gold Nanohole Array Substrates as Immunobiosensors", Analytical Chemistry, American Chemical Society, vol. 80, No. 6, Mar. 15, 2008, pp. 2244-2249.
Nanoparticle Analyzer, Nano Partica SZ-100 Series Brochure, Horiba Scientific, accessed Mar. 21, 2019, http://www.horiba.com/scientific/products/particle-characterization/particle-size-analysis/details/sz-100-7245/?referrer=AZONANO, 8 pages.
Anker, Jeffrey N., et al., "Biosensing with plasmonic nanosensors," Nanoscience and Technology: A Collection of Reviews from Nature Journals, World Scientific, 2010, pp. 308-319.
Baaske, Martin D., et al., "Single-molecule nucleic acid interactions monitored on a label-free microcavity biosensor platform," Nature Nanotechnology, vol. 9, No. 11, Nov. 2014, pp. 933-939.
Ballard, Zachary S., et al., "Computational Sensing Using Low-Cost and Mobile Plasmonic Readers Designed by Machine Learning," ACS Nano 2017, vol. 11, No. 2, pp. 2266-2274.
Belushkin, Alexander, et al., "Rapid and Digital Detection of Inflammatory Biomarkers Enabled by a Novel Portable Nanoplasmonic Imager," Small 2020, vol. 16, 1906108, 11 pages.
Bergeret, Gérard, et al., "Particle Size and Dispersion Measurements," Handbook of Heterogeneous Catalysis Online, 2008, pp. 738-765.
Black, Steven, et al., "C-reactive Protein," The Journal of Biological Chemistry, vol. 279, No. 47, Nov. 19, 2004, pp. 48487-48490.
Bozhevolnyi, Sergey I., et al., "Channel plasmon subwavelength waveguide components including interferometers and ring resonators," Nature, vol. 440, No. 7083, Mar. 23, 2006, pp. 508-511.
Brolo, Alexandre G., et al., "Surface Plasmon Sensor Based on the Enhanced Light Transmission through Arrays of Nanoholes in Gold Films," Langmuir, vol. 20, No. 12, 2004, pp. 4813-4815.
Cetin, Arif E., et al., "Handheld high-throughput plasmonic biosensor using computational on-chip imaging," Light: Science & Applications, vol. 3, No. 1, e122, 2014, 10 pages.
Cetin, Arif E., et al., "Plasmonic Nanohole Arrays on a Robust Hybrid Substrate for Highly Sensitive Label-Free Biosensing," ACS Photonics, vol. 2, No. 8, 2015, pp. 1167-1174.
Coskun, Ahmet F., et al., "Lensfree optofluidic plasmonic sensor for real-time and label-free monitoring of molecular binding events over a wide field-of-view," Scientific Reports, vol. 4, 6789, 7 pages.
Couture, Maxime, et al., "96-Well Plasmonic Sensing with Nanohole Arrays," ACS Sensors, vol. 1, No. 3, 2016, pp. 287-294.
Dantham, V. R., et al., "Taking whispering gallery-mode single virus detection and sizing to the limit," Applied Physics Letters, vol. 101, No. 4, 2012, pp. 043704-1-043704-5.
Dellinger, R. P., et al., "Surviving Sepsis Campaign: International Guidelines for Management of Severe Sepsis and Septic Shock, 2012," Intensive Care Med, vol. 39, No. 2, 2013, pp. 165-228.
Dickson, Robert M., et al., "On/off blinking and switching behaviour of single molecules of green fluorescent protein," Nature, vol. 388, No. 6640, Jul. 24, 1997, pp. 355-358.
Di Fabrizio, Enzo, et al., "Roadmap on biosensing and photonics with advanced nano-optical methods," Journal of Optics, vol. 18, No. 6, 063003, 2016, 27 pages.
Ebbesen, T. W., et al., "Extraordinary optical transmission through sub-wavelength hole arrays," Nature, vol. 391, No. 6668, Feb. 12, 1998, pp. 667-669.
Fan, Xudong, et al., "Sensitive optical biosensors for unlabeled targets: A review," Analytica Chimica Acta, vol. 620, No. 1, 2008, pp. 8-26.
Harris, Tamara B., et al., "Associations of Elevated Interleukin-6 and C-Reactive Protein Levels with Mortality in the Elderly," The American Journal of Medicine, vol. 106, No. 5, May 1999, pp. 506-512.
Homola, Jiří, "Surface Plasmon Resonance Sensors for Detection of Chemical and Biological Species," Chemical Reviews, vol. 108, No. 2, 2008, pp. 462-493.
Im, Hyungsoon, et al., "Label-free detection and molecular profiling of exosomes with a nano-plasmonic sensor," Nature Biotechnology, vol. 32, No. 5, May 2014, pp. 490-495.
Jackman, Joshua A., et al., "Plasmonic Nanohole Sensor for Capturing Single Virus-Like Particles toward Virucidal Drug Evaluation," Small 2016, vol. 12, No. 9, pp. 1159-1166.
Jain, Ankur, et al., "Probing cellular protein complexes using singe-molecule pull-down," Nature, vol. 473, No. 7348, May 26, 2011, pp. 484-488.
Kabashin, A. V., et al., "Plasmonic nanorod metamaterials for biosensing," Nature Materials, vol. 8, No. 11, Nov. 2009, pp. 867-871.
Kosaka, P. M., et al., "Detection of cancer biomarkers in serum using a hybrid mechanical and optoplasmonic nanosensor," Nature Nanotechnology, vol. 9, No. 12, Dec. 2014, pp. 1047-1053.
Li, Xiaokang, et al., "Plasmonic nanohole array biosensor for label-free and real-time analysis of live cell secretion," Lab Chip, vol. 17, 2017, pp. 2208-2217.
Lindquist, Nathan C., et al., "Engineering metallic nanostructures for plasmonics and nanophotonics," Reports on Progress in Physics, vol. 75, No. 3, 036501, 2012, 61 pages.
Lopez, Gerardo A., et al., "Recent advances in nanoplasmonic biosensors: applications and lab-on-a-chip integration," Nanophotonics, vol. 6, No. 1, pp. 123-136.
Mazzotta, Francesco, et al., "Influence of the Evanescent Field Decay Length on the Sensitivity of Plasmonic Nanodisks and Nanoholes," ACS Photonics, vol. 2, No. 2, 2015, pp. 256-262.
Najiminaini, Mohamadreza, et al., "Nanohole-array-based device for 2D snapshot multispectral imaging," Scientific Reports, vol. 3, No. 2589, 2013, 7 pages.
Niu, Rui, et al., "iTRAQ-Based Proteomics Reveals Novel Biomarkers for Idiopathic Pulmonary Fibrosis, " PLOS One, vol. 12, No. 1, e0170741, 2017, 18 pages.
Pradhan, Aruna D., et al., "C-Reactive Protein, Interleukin 6, and Risk of Developing Type 2 Diabetes Mellitus," The Journal of the American Medical Association, vol. 286, No. 3, Jul. 18, 2001, pp. 327-334.
Raether, H., "Surface Plasmons on Smooth Surfaces," Springer, 1988, pp. 4-39.
Ridker, Paul M., et al., "C-Reactive Protein Levels and Outcomes after Statin Therapy," The New England Journal of Medicine, vol. 352, No. 1, Jan. 6, 2005, pp. 20-28.
Ridker, Paul M., et al., "Rosuvastatin to Prevent Vascular Events in Men and Women with Elevated C-Reactive Protein," The New England Journal of Medicine, vol. 359, No. 21, Nov. 20, 2008, pp. 2195-2207.

(56) References Cited

OTHER PUBLICATIONS

Rissin, David M., et al., "Single-molecule enzyme-linked immunosorbent assay detects serum proteins at subfemtomolar concentrations," Nature Biotechnology, vol. 28, No. 6, Jun. 2010, pp. 595-599.
Sharpe, John C., et al., "Gold Nanohole Array Substrates as Immunobiosensors," Analytical Chemistry, vol. 80, No. 6, Mar. 15, 2008, pp. 2244-2249.
Shen, Yang, et al., "Plasmonic gold mushroom arrays with refractive index sensing figures of merit approaching the theoretical limit," Nature Communications, vol. 4, 2381, Aug. 27, 2013, 9 pages.
Simon, Liliana, et al., "Serum Procalcitonin and C-Reactive Protein Levels as Markers of Bacterial Infection: A Systematic Review and Meta-analysis," Clinical Infectious Diseases, vol. 39, No. 2, Jul. 15, 2004, pp. 206-217.
Soler, Maria, et al., "Multiplexed nanoplasmonic biosensor for one-step simultaneous detection of Chlamydia trachomatis and Neisseria gonorrhoeae in urine," Biosensors and Bioelectronics, vol. 94, 2017, pp. 560-567.
Breekanth, Kandammathe Valiyaveedu, et al., "Extreme sensitivity biosensing platform based on hyperbolic metamaterials," Nature Materials, vol. 15, No. 6, Jun. 2016, pp. 621-627.
Su, Judith, et al., "Label-free detection of single nanoparticles and biological molecules using microtoroid optical resonators," Light: Science & Applications, vol. 5, No. 1, e16001, 2016, 6 pages.
Unser, Sarah, et al., "Localized Surface Plasmon Resonance Biosensing: Current Challenges and Approaches," Sensors, vol. 15, No. 7, 2015, pp. 15684-15716.
Walt, David R., "Optical Methods for Single Molecule Detection and Analysis," Analytical Chemistry, vol. 85, 2013, pp. 1258-1263.
Wood, R. W., "On a Remarkable Case of Uneven Distribution of Light in a Diffraction Grating Spectrum," Proceedings of the Physical Society of London, vol. 18, 1902, pp. 269-275.
Yanik, Ahmet A., et al., "An Optofluidic Nanoplasmonic Biosensor for Direct Detection of Live Viruses from Biological Media," Nano Letters, vol. 10, No. 12, 2010, pp. 4962-4969.
Yesilkoy, Filiz, et al., "Phase-sensitive plasmonic biosensor using a portable and large field-of-view interferometric microarray image," Light: Science & Applications, vol. 7, 17152, 2018, 9 pages.
Zeng, Shuwen, et al., "Nanomaterials enhanced surface plasmon resonance for biological and chemical sensing applications," Chemical Society Reviews, vol. 43, No. 10, 2014, pp. 3426-3452.
Zheng, Tianyu, et al., "Techniques for Accurate Sizing of Gold Nanoparticles Using Dynamic Light Scattering with Particular Application to Chemical and Biological Sensing Based on Aggregate Formation," ACS Applied Materials & Interfaces, vol. 8, No. 33, 2016, pp. 21585-21594.
Zijlstra, Peter, et al., "Optical detection of single non-absorbing molecules using the surface plasmon resonance of a gold nanorod," Nature Nanotechnology, vol. 7, No. 6, Jun. 2012, pp. 379-382.
Csáki, Andrea, et al., "Combination of Nanoholes with Metal Nanoparticles—Fabrication and Characterization of Novel Plasmonic Nanostructures", Plasmonics, vol. 1, No. 2-4, 2006, pp. 147-155.
Communication pursuant to Article 94(3) EPC dated Jun. 18, 2024, issued in European Application No. 19721778.9, 6 pages.

\* cited by examiner

PLASMONIC BIOSENSOR

CROSS-REFERENCE TO RELATED APPLICATIONS

This application is the U.S. national phase of International Application No. PCT/IB2019/052475 filed Mar. 27, 2019 which designated the U.S. and claims the benefit of U.S. Provisional Application No. 62/648,462 filed Mar. 27, 2018, the entire contents of each of which are hereby incorporated by reference.

FIELD OF THE INVENTION

The present disclosure relates to a plasmonic biosensor system or device. The present disclosure concerns a plasmonic biosensor system or device for biomarker detection and, in particular, a nanoparticle or nanoparticle enhanced plasmonic biosensor for biomarker detection (or digital biomarker detection) in a microarray. The present disclosure also concerns a plasmonic bio-sensing method.

BACKGROUND

Nanophotonic devices provide a prominent toolbox for biosensing applications in the fields from biological and pharmaceutical research to medical diagnostics and global health due to their capacity for highly sensitive and multiplexed biodetection from small sample volumes in a compact footprint. In particular, nanoplasmonic devices have become a paradigm for biomolecular detection enabled by enhanced light-matter interactions, however, their requisite detection sensitivity usually comes at the cost of optical complexity of the readers.

Nanophotonics is offering new opportunities to realize high performance biosensors for the fields ranging from biological and pharmaceutical research to medical diagnostics and global healthcare.[1-5] For instance, the management of acute diseases such as inflammation and infections[6] or chronic conditions such as cancer[7] could benefit profoundly from rapid, sensitive and cost-effective on-site diagnostic tools. Conventional laboratory techniques, such as enzyme-linked immunosorbent assay (ELISA)[8] and fluorescent labelling[9,10] can achieve relevant sensitivity levels of molecular detection, however they require complex optical read-out, multiple incubation-washing steps and fluorescent tags that can be expensive, unstable and difficult to produce.

Nanophotonic resonators can efficiently funnel light into nano-scale volumes compatible with biomolecule dimensions, thereby strongly enhance light-matter interactions and transduce molecular surface binding events into far-field optical signals.[11] The high sensitivity of nanophotonic biosensors combined with the scalability of detection schemes, low-cost operation and capability for multiplexed measurements make them prominent for various biosensing applications. Among the recent ones, optical nanobiosensors based on whispering gallery mode[12,13] and hyperbolic metamaterials[14] were shown to provide some of the highest sensitivities down to single-molecule detection.[15] However, these techniques require complex and bulky read-out set-ups, intricate fabrication procedures and have limited scalability hindering their use as cost-effective and multiplexed biosensors.

On the other hand, nanoplasmonic resonators, made of noble metals, couple the photon energy to the collective oscillations of the metal's free electrons, also known as surface plasmons, which interact with the biomolecules at the metal surface.[16] A number of nanoplasmonic devices have been engineered to efficiently probe the local refractive index variations upon the biomolecular surface binding events yielding high refractometric sensitivities.[14,17-20] So far, both the propagating (SPR)[21] and localized surface plasmons (LSPR)[22,23] have been widely explored for biosensing applications. Particularly, the Au nanohole arrays (Au-NHA) have been prominent plasmonic systems because they can be operated in a robust collinear optical configuration allowing integration in low-cost, easy-to-use, and portable platforms.[24-27] The periodic Au-NHAs exhibit a sharp extraordinary optical transmission (EOT) resonance associated with a dip and a peak in the far-field spectrum due to the interplay of coherently interfering resonant interactions and grating effects (see, for example, FIG. 2EI.).[28]

Previously, Au-NHAs were explored for numerous biosensing applications ranging from the detection of proteins[29,30] to exosomes,[31] viruses,[32,33] bacteria[34] and cell secretion,[35] mainly based on spectral data monitoring. In an attempt to miniaturize the Au-NHA based biosensors, intensity imaging in transmission was used to detect the shifts of the EOT peak without the need of a spectrometer.[24-26] Intensity imaging enables 2D large-area detection and can be performed using a narrowband illumination source, such as an LED, tuned to the EOT peak to monitor variations in the transmittance due to the spectral shift of the resonance (see, for example, FIG. 2E II.). Although the approach can be realized with a 2D image sensor array, such as charge-coupled device (CCD) or complementary metal-oxide-semiconductor (CMOS), on a portable optical reader, its previous implementation[25] using Au-NHAs could only achieve detection of 4 µg/ml protein, significantly above the relevant clinical concentrations of most biomarkers.

In these conventional spectroscopic and imaging read-out schemes, the signal transduction relies on the spectral shifts in plasmonic transmission resonances due to refractive index changes induced by the formation of an analyte monolayer with a certain layer density and thickness. Consequently, the sensitivity levels of such approaches are inherently limited by the concentration and the size of the analyte molecules, as well as non-specific interactions from complex samples.

SUMMARY OF THE INVENTION

It is thus a goal of the present disclosure to address the above-mentioned inconveniencies.

The present invention addresses the above-mentioned limitations by providing a plasmonic biosensor Including a nano-hole array device comprising at least one nano-hole array including a plurality of nano holes, the at least one nano-hole array being able to be functionalized to capture a target antigen or biomarker, and at least one or a plurality of nano-particles configured to be received by the nano-holes of the nano-hole array, the at least one or the plurality of nano-particles comprising or consisting solely of at least one metal and the at least one or the plurality of nano-particles being able to be functionalized with at least one molecule configured to bind or conjugate to a target antigen or biomarker.

The plasmonic biosensor may further include an image sensor for capturing light, provided by a light source for illuminating the nano-hole array, transmitted through the nano-hole array.

Other advantageous features can be found in the dependent claims.

The plasmonic biosensor of the present disclosure allows visualization of single sub-wavelength nanoparticles (NPs), for example gold nanoparticles, on large-area nanohole arrays NHAs (for example, gold nanohole arrays) on a simple bright-field imager. This sensor can generate image maps or heatmaps, which reveal the locations of single NPs as high-contrast spikes, thus enabling the detection of individual nanoparticle-labeled molecules. In contrast to conventional plasmonic biosensors, which monitor spatially averaged signals from spectral resonance shifts, the technique of the present disclosure exploits the digital quantification and localization of distinctive local extraordinary optical transmission quenching on NHAs caused by individual NPs, associated to single molecule binding.

The system/device and method of the present disclosure has been implemented, for example, in a sandwich immunoassay for the detection of biotinylated bovine serum albumin (bBSA) and human C-reactive protein (CRP), a clinical biomarker of acute inflammatory diseases. This system and method can detect 10 pg/ml of bBSA and 27 pg/ml CRP in 2 hours, which is at least four orders of magnitude lower than the clinically relevant concentrations. This sensitive and rapid detection approach paired with the robust large-area plasmonic sensor chips, which are fabricated using scalable and low-cost manufacturing, provides a powerful platform for multiplexed biomarker detection in various settings.

The present disclosure presents a nanoparticle enhanced imaging-based plasmonic biosensing technique or system using NHAs, for example, Au-NHAs that enables for example highly sensitive protein detection with single analyte resolution. By digital quantification and localization of individual Au-NPs (for example, of 100 nm diameter) under bright-field imaging on large area plasmonic imaging surface, the technique enables the detection of single nanoparticle-labeled proteins. The technique is implemented, for example, in a one-step sandwich immunoassay. After being captured by the first (capture) antibody immobilized on plasmonic NHAs (for example, Au NHAs), the protein biomarker is recognized by a second (detection) antibody conjugated to Au-NPs in solution (see, for example, FIG. 1A). Upon binding to the analyte, NPs locally disturb the near-fields of the NHAs (see, for example, FIG. 2E III.), leading to a strong local transmission suppression in the far-field. These distortions in the transmission from the small vicinity of the NPs are detected under narrow-band illumination at the EOT peak in the visible range (FIGS. 1B and 1C), creating plasmonic intensity heatmaps that allow visualization of individual nanoparticle-labeled analytes as high contrast spots.

The Inventors applied this novel and innovate biosensing approach in a proof-of-principle detection of biotinylated bovine serum albumin (bBSA, 67 kDA) and then human C-reactive protein (CRP, 100 kDA), a well-established biomarker used for clinical diagnosis and management of acute inflammatory diseases[36-39]. The Inventors show that the approach of the present disclosure enables the detection of bBSA down to 10 pg/ml and CRP down to 27 pg/ml limit-of-detection (LOD). This result is at least four orders of magnitude below CRP levels determining patients at high risk of inflammatory diseases[40,41] and is well comparable to the established fluorescence amplification techniques, such as ELISA.[42]

At the same time, the technique of the present disclosure avoids lengthy signal amplification steps and the plasmonic chips and NPs are stable over time, unlike fluorescence labels that experiences photobleaching. In addition, the plasmonic signals are highly confined at the sensor interface and are unaffected by the bulk background, which enables the method to be used in real-time measurements. Importantly, the NHA sensors, such as the Au-NHA sensors, are fabricated using low-cost wafer-scale deep-UV lithography (DUVL) producing exceedingly robust and uniform large-area chips on solid transparent substrates (see, for example, FIG. 1D).[43] In combination with a simple bright-field imaging set-up in a microarray format, the biosensing technology of the present disclosure can be scaled to perform clinically relevant biomarker detection in a highly multiplexed manner.

The above and other objects, features and advantages of the present invention and the manner of realizing them will become more apparent, and the invention itself will best be understood from a study of the following description with reference to the attached drawings showing some preferred embodiments of the invention.

A BRIEF DESCRIPTION OF THE SEVERAL VIEWS OF THE DRAWINGS

FIG. 1 generally shows an exemplary nanoparticle enhanced plasmonic imager for digital biomarker detection. FIG. 1A shows an antigen recognized by capture antibodies immobilized on the Au-NHA and then by detection antibodies tethered to Au-NPs. FIG. 1B shows strong local suppression in the transmission by Au-NPs creating intensity dips at the corresponding locations of the captured image. FIG. 1C shows an exemplary bright-field imaging set-up under narrow-band illumination at the Au-NHA EOT resonance to detect distortions in transmission from plasmonic NHA chip. For more accurate image processing, the biosensor chip is for example patterned with microarray labels. The CMOS camera displays transmission signal as an image heatmap enabling digital detection of biomolecules. FIG. 1D shows Left to Right: an exemplary Au-NHA wafer with 50 sensor chips robustly fabricated using scalable low-cost techniques. Au-NHAs uniformly cover the entire plasmonic sensor surface. SEM of a post-patterned chip with microarray marks. SEM of Au-NHAs (Diameter D=200 nm, Period P=600 nm) with a single Au-NP bound in a hole. Side-view SEM of two neighbouring nanoholes with a NP inside one of the nanoholes.

Figure 2:
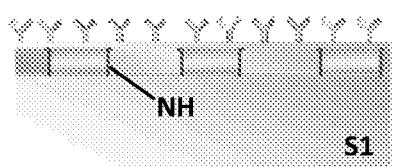
Figure 2:
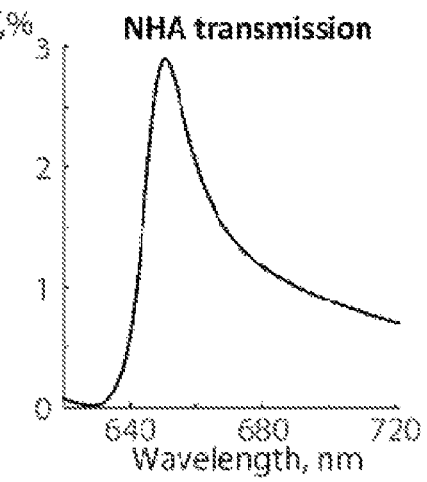
Figure 2:
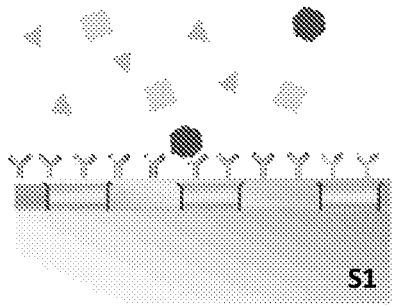
Figure 2:
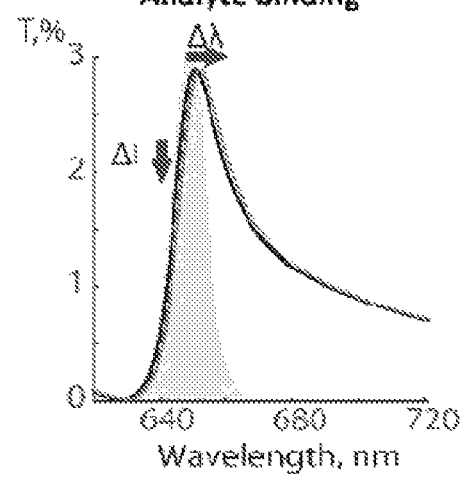
Figure 2:
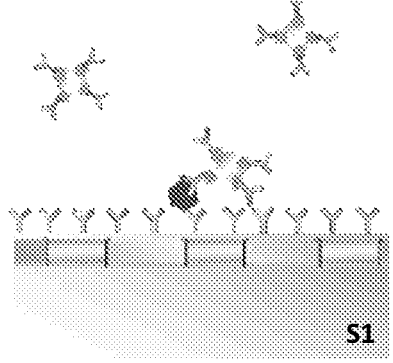
Figure 2:
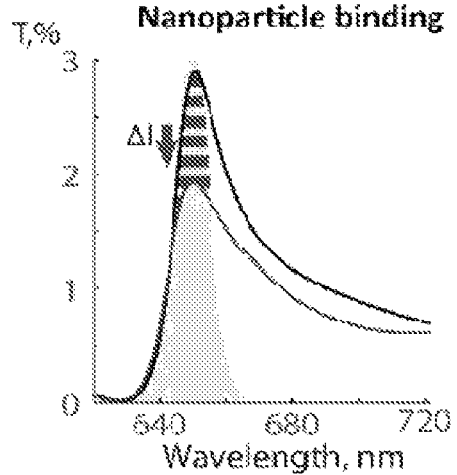

FIG. 2 shows I. Simulated transmission spectrum of exemplary Au-NHAs exhibiting EOT peak at 650 nm in air; II. Biomolecule binding causes minuscule spectral shifts in peak position; and III. Binding of Au-NPs to the Au-NHA surface results in strong local suppression of the EOT peak.

Figure 3:
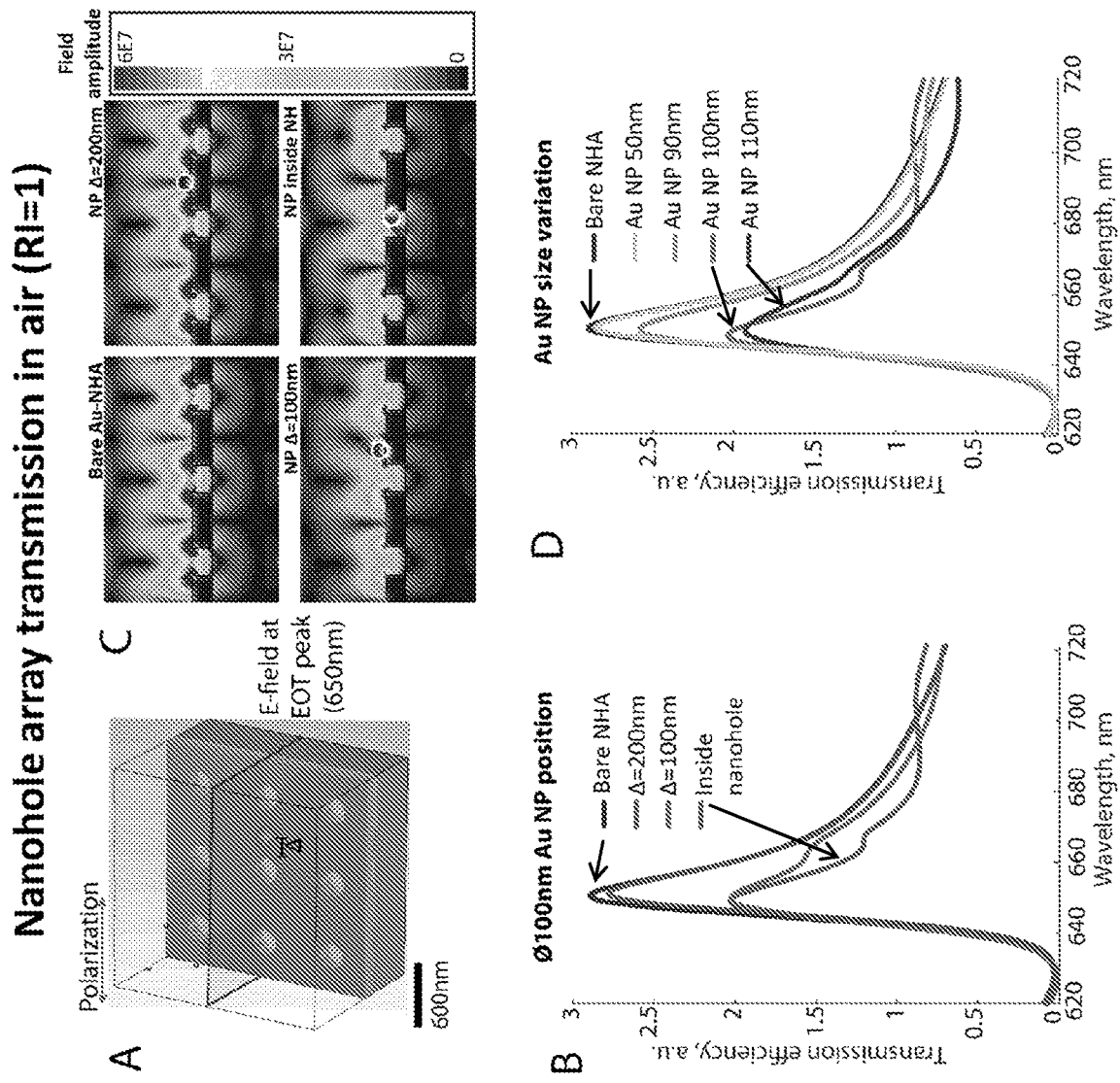

FIG. 3 shows simulated transmission spectra and electric near-field maps of exemplary Au-NHAs distorted by Au-NPs. FIG. 3A shows a unit cell of 3×3 nanohole array (Diameter=200 nm, Period=600 nm) used in the FEFD simulations excited from top with TM mode and using periodic boundary conditions. FIG. 3B shows Au-NP position dependent EOT transmission spectra of Au-NHAs. The peak suppression increases when Au-NP is bound inside the NH or close to the NH rim and is minimally affected when placed far from the NH. FIG. 3C shows cross-sections of Au-NHA E-field maps at the EOT resonance (650 nm). When Au-NPs are inside or close to the NH the LSP modes are disturbed strongly, locally suppressing the transmission. FIG. 3D shows that the transmission suppression increases with the NP diameter, saturating at 100 nm in this exemplary embodiment.

Figure 4:
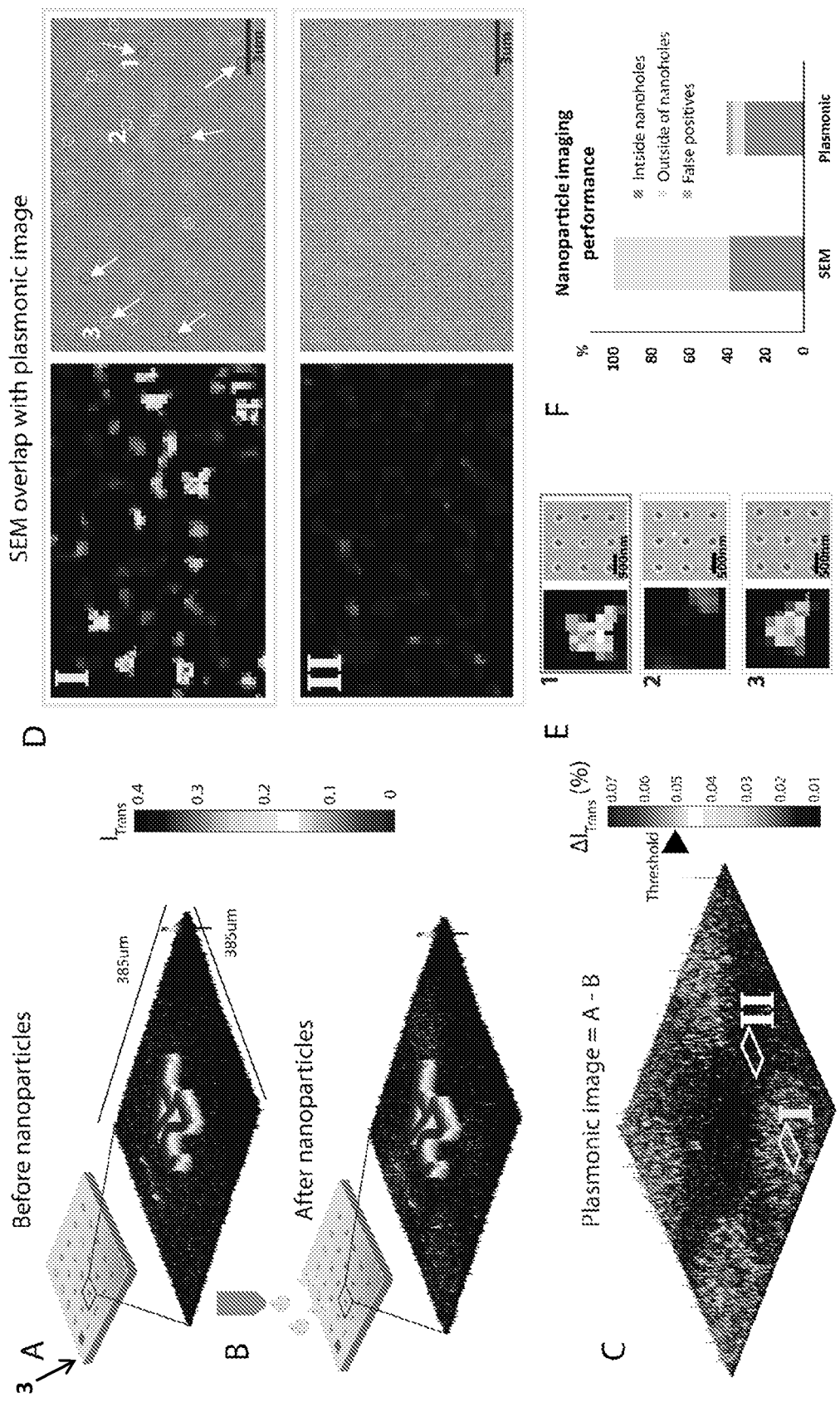

FIG. 4 shows bright-field plasmonic imaging of exemplary Au NPs and SEM validation. FIG. 4A shows reference images of bare Au-NHAs with alignment microarray labels. FIG. 4B shows Au-NHAs imaged after Au-NPs binding at the same microarray elements shown in FIG. 4A. FIG. 4C shows the microarray field to contain 2×2 arrays of sensing spots and shows a color-coded surface plot of transmission intensity spikes caused by NPs formed by computational alignment and subtraction of FIG. 4B from FIG. 4A producing an image heatmap. FIG. 4D Left: Computed plasmonic images of Au-NHA areas. Right: Plasmonic images overlapped with the SEMs of identical regions with NPs (I) and without NPs (II), zoomed out from FIG. 4C. The NPs inside NHs are marked by dark circles and NPs outside NHs with lighter circles. FIG. 4E shows Au-NPs inside nanoholes producing strong intensity changes (1) and can be detected. NPs far from NHs cannot be detected by plasmonic imaging (2). A fraction of NPs bound close to the NHs rim produces a sufficient intensity change to be identified by the plasmonic imaging (3). FIG. 4F shows that in the experiments, statistically 40% of NPs are bound inside and 60% outside of NHs (1000 NPs sample size, verified by SEM). Plasmonic imaging correctly identifies around 40% of NPs, while false positive signals are 3% (sample of 127 NPs).

Figure 5:
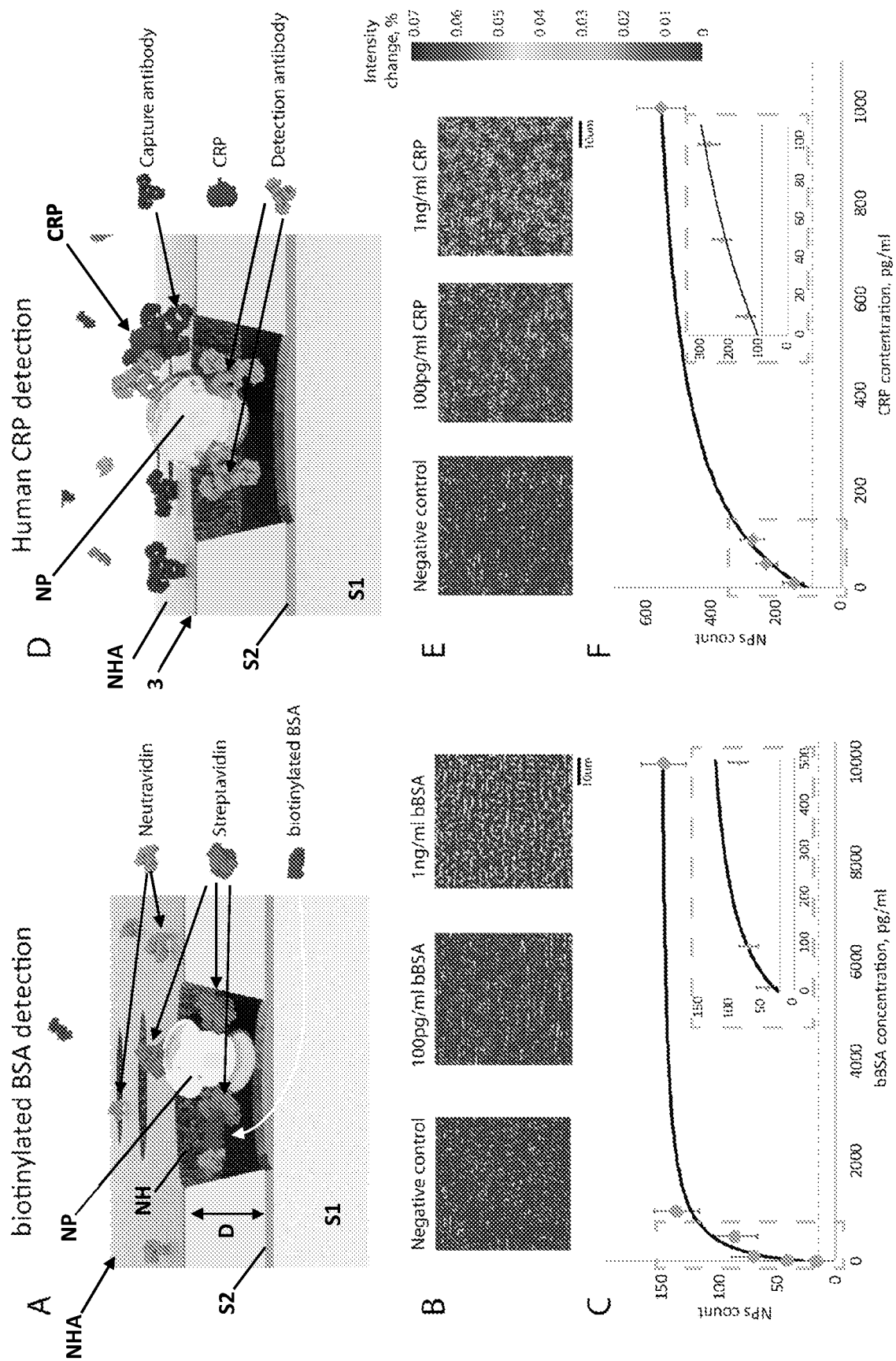

FIG. 5 shows nanoparticle enhanced digital protein detection. FIG. 5A is an Illustration of bBSA sandwich assay. FIG. 5B shows that different concentrations of bBSA are detected as different densities of NPs are seen on plasmonic heatmap images. FIG. 5C shows a bSBA calibration curve (LOD=10 pg/ml). FIG. 5D shows a Human CRP sandwich assay. FIG. 5E shows that different concentrations of CRP can be visually distinguished on plasmonic imaging. FIG. 5F shows Human CRP calibration, (LOD=27 pg/ml).

Figure 6:
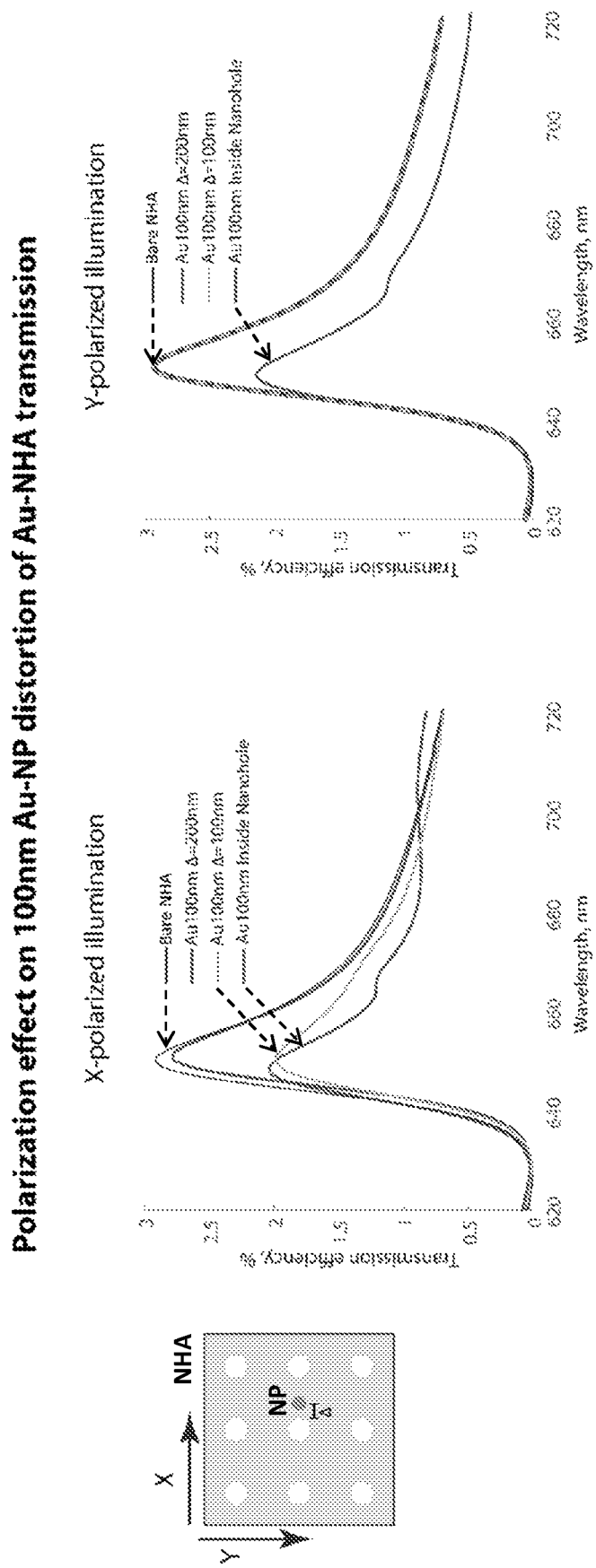

FIG. 6 shows a polarization effect on transmission suppression produced by a 100 nm Au NP on Au-NHA transmission. NP bound inside a NH affects localized modes in all directions (X-polarized and Y-polarized). NP that is on the surface close to the NH rim efficiently suppresses transmission of light polarized in one direction (X-polarized) but has no effect in the orthogonal direction.

Figure 7:
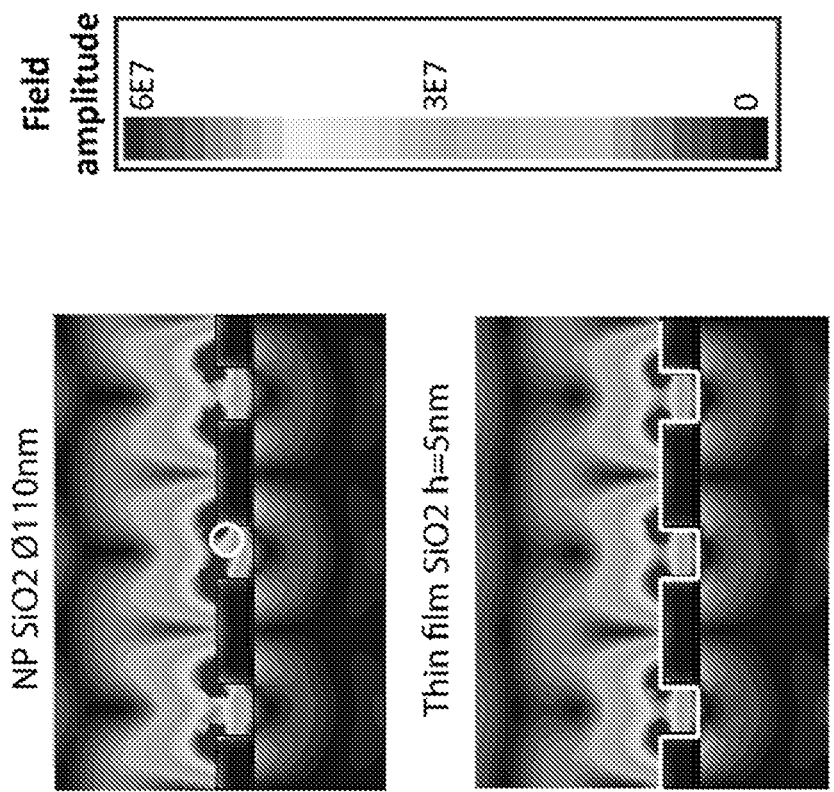
Figure 7:
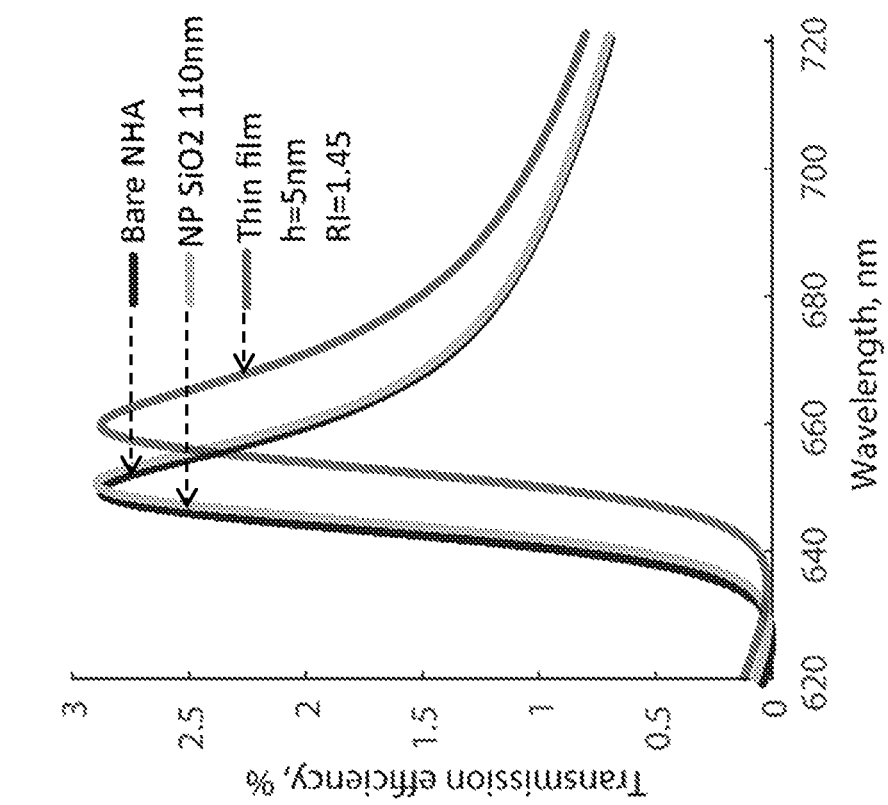

FIG. 7 shows a dielectric NP and thin-film effect on Au-NHA transmission. A $SiO_2$ nanoparticle has very little effect on Au-NHA transmission, causing small effective refractive changes, but does not disrupt the formation of localized plasmonic nanohole modes. A $SiO_2$ thin film of 5 nm height causes spectral shift of Au-NHA transmission resonance peak due to refractive index changes.

Figure 8:
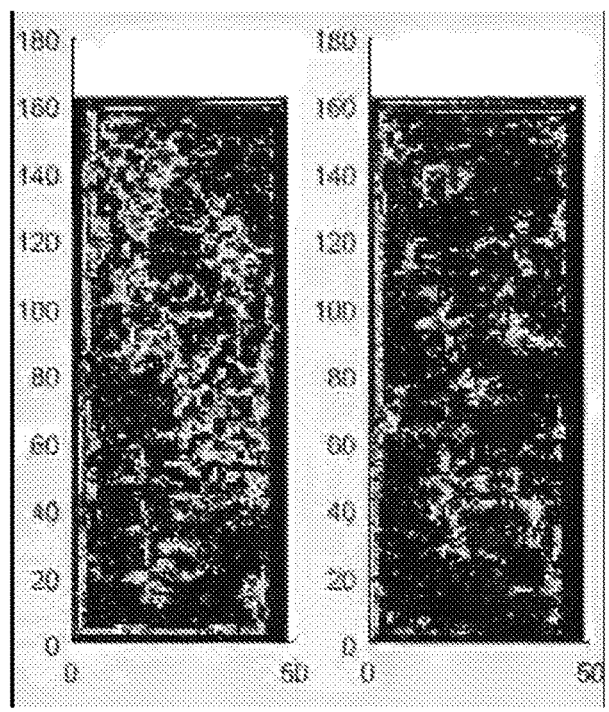

FIG. 8 shows the resulting image after real-time imaging of 100 nm Au-NPs binding to Au-NHA sensors (100×300 $\mu m^2$). Two different areas are shown under narrow-band illumination at the EOT peak of Au-NHAs in aqueous medium (850 nm). Au-NHA was functionalized with biotinylated thiols and streptavidin-conjugated NPs were introduced in-flow using a microfluidic PDMS chip assembled over the Au-NHA chip. Because the Au-NHA plasmon modes are highly confined at the sensor chip interface, the bulk background during NPs injection does not affect the imaging of surface binding events.

Figure 9:
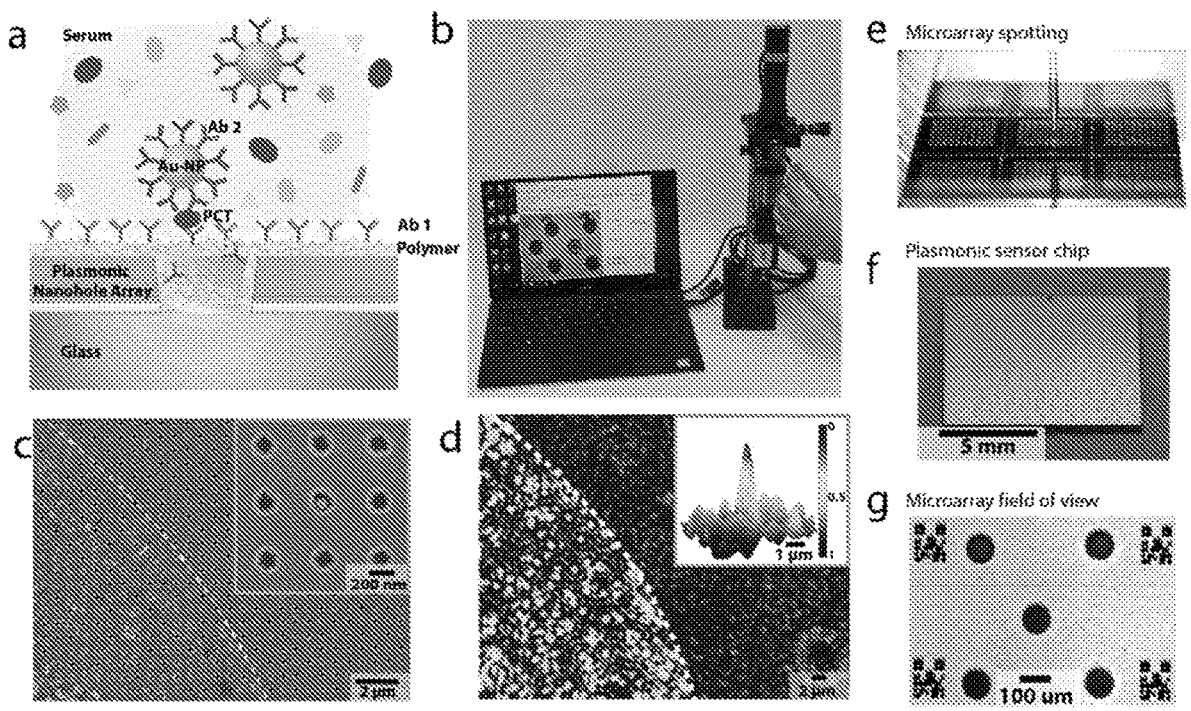

FIG. 9 shows an exemplary digital nanoparticle-enhanced nanoplasmonic imager for sepsis (DENIS) detection. FIG. 9(a) shows PCT and CRP, which are blood-circulating protein biomarkers secreted by a host body in response to systemic inflammation, detected using DENIS. A single-step bioassay directly in human serum enables rapid molecular results, critical for the early diagnosis of sepsis, by detecting individual nanoparticles (NPs) binding to gold plasmonic nanohole arrays (Au-NHA). FIG. 9b shows an exemplary DENIS reader developed for highly sensitive and multiplexed detection of biomarkers. The device comprises, for example, a CMOS camera and a narrow-band LED source to record the transmitted images from a nanoplasmonic chip. FIG. 9c is a SEM image of a Au-NHA area after a bioassay showing the bound NPs. The inset shows a single nanoparticle bound inside a nanohole. FIG. 9d shows a plasmonic image of an exemplary Au-NHA area with bound nanoparticles. The binding of Au-NPs on Au-NHAs causes local transmission suppression through distortion of plasmonic excitations in the Au-NHA, and can be digitally detected using far-field imaging. The inset shows a normalized intensity contrast induced by a single nanoparticle trapped in a nanohole. FIG. 9e shows that to enable microarray based biosensing, capture antibodies can be immobilized on the Au-NHA sensor surface using non-contact ultra-low volume robotic liquid dispenser. The image shows 9 sensor chips with spotted microarrays under dispensing nozzle. FIG. 9f is a photograph of an Au-NHA plasmonic chip. The sensors are fabricated using, for example, wafer-scale DUVL lithography. FIG. 9g is an image of a plasmonic microarray field of view with antibody spots, and labelled with QR codes.

Figure 10:
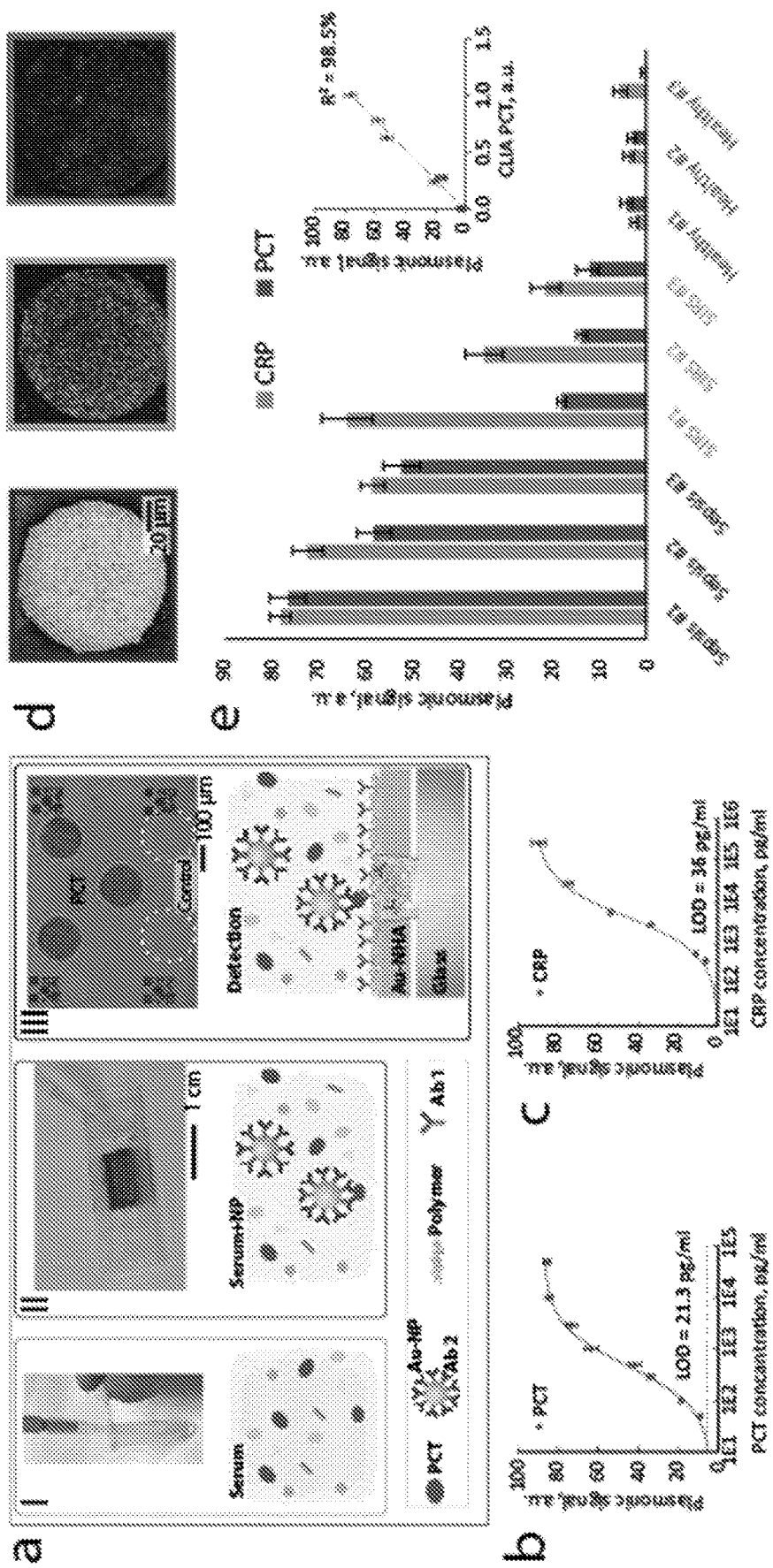

FIG. 10 shows sepsis biomarker detection and quantification using DENIS. In FIG. 10a, a serum sample (I) is mixed with Au-NPs functionalized with antibodies against PCT or CRP (Ab-NPs). Ab-NPs bind to the antigen in serum (II). Sample with Ab-NPs is injected on Au-NHA sensor chip functionalized with polymer and spots of complementary aPCT or aCRP antibodies as well as non-specific mouse IgG as negative control. Ab-NPs bind on the Au-NHA chip functionalized with complementary antibody spots in a sandwich assay in the presence of the antigen (III). FIGS. 10b and 10c show the determining of the detection sensitivity for PCT and CRP biomarkers with the DENIS system. The calibration curves were obtained by titrating a known concentration of PCT or CRP and measuring the associated signal. FIG. 10d shows that different concentration of PCT in serum results in different density of particle binding. From left to right: representative microspots imaged from clinical samples associated to a sepsis patient, a SIRS patient, and a healthy donor are shown. FIG. 10e shows the quantification of PCT and CRP biomarkers using DENIS in the serum of typical representative patients with sepsis, SIRS and healthy controls. Error bars represent standard deviation between signals of five spots measured for each sample. The inset shows correlation between DENIS and CLIA measurements of PCT levels for the typical patients.

Figure 11:
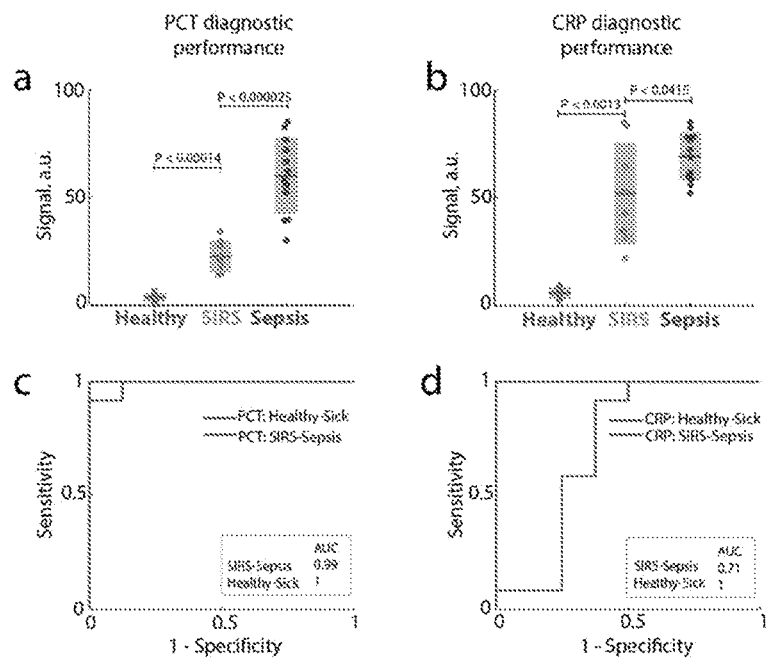

FIG. 11 shows PCT and CRP as diagnostic biomarkers to discriminate sepsis and SIRS using DENIS. Samples from 25 clinically diagnosed individuals, including 12 sepsis patients, 8 SIRS patients, and 5 healthy controls, were tested. Box and whiskers plot with scattered data points for sepsis, SIRS and healthy samples are shown for (a) PCT and (b) CRP analysis. Each data point represents an individual patient. PCT and CRP serum levels were significantly higher for SIRS group compared to healthy ($P<0.00014$ and $P<0.0013$, respectively). The difference between sepsis and SIRS groups was a lot more significant for PCT levels than CRP ($P<0.000025$ and $P<0.0415$, respectively). Receiver-operation characteristic curves were constructed for PCT (c) and CRP (d). The AUC is 1 for both PCT and CRP to discriminate healthy from sick patients. PCT levels provide better classification between SIRS and sepsis patients compared to CRP. With PCT, AUC=0.99, Sensitivity=1, and Specificity=0.875, whereas with CRP, AUC=0.71, Sensitivity=0.92 and Specificity=0.625.

Figure 12:
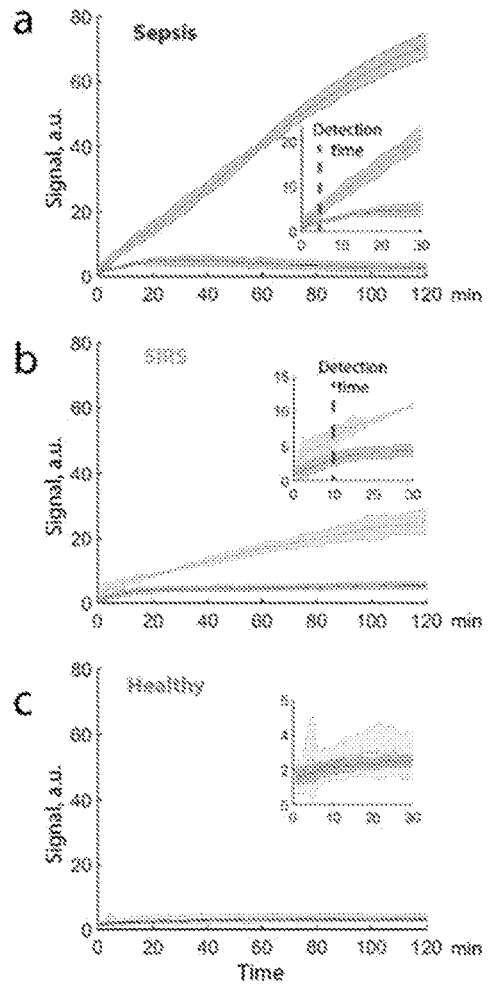

FIG. 12 shows time resolved PCT detection using DENIS. Real-time measurements of selected subjects: (a) sepsis patient, (b) SIRS patient and (c) healthy control. Error bars from the PCT signal represent 95% confidence interval extracted from data collected from three different aPCT microspots from a single image frame. The background signals are collected from three off-the spot BSA blocked areas. The blue shaded intervals indicate dynamic time averaged 95% confidence interval for background signal. Insets show the first 30 min time period. The detection time is defined as the cut-off point when the PCT signal's 95% lower confidence interval exceeds the background's upper confidence interval. The detection time is estimated to be less than 5 mins for sepsis and 10 mins for SIRS.

Figure 13:
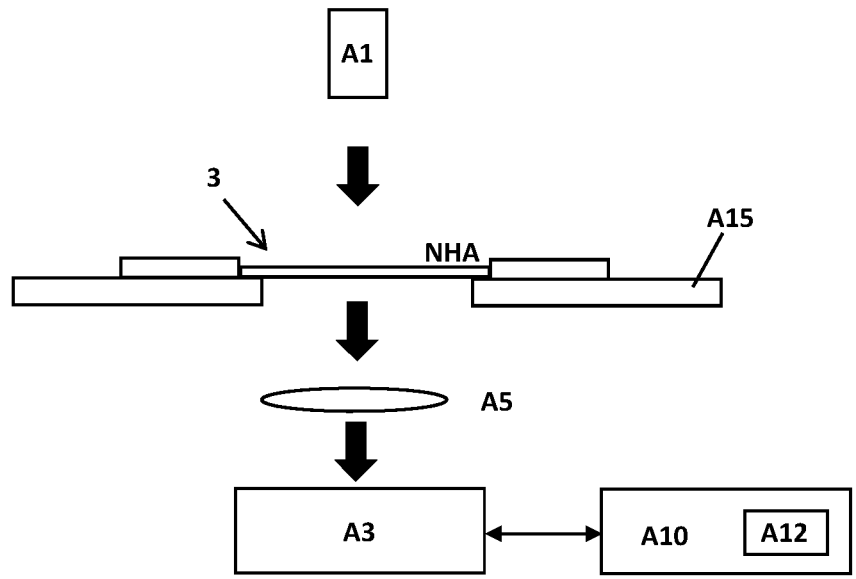
Figure 14:
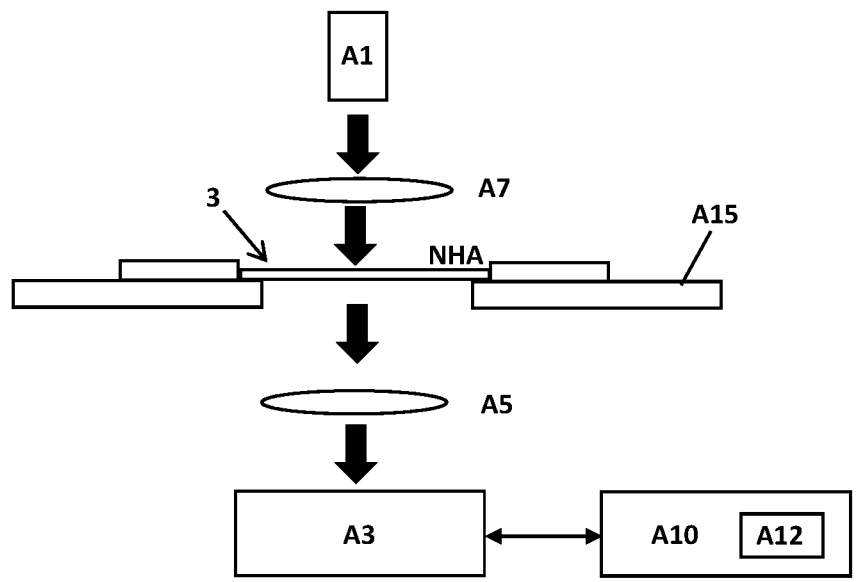

FIGS. 13 and 14 schematically show exemplary plasmonic biosensor systems according to the present disclosure.

Figure 15:
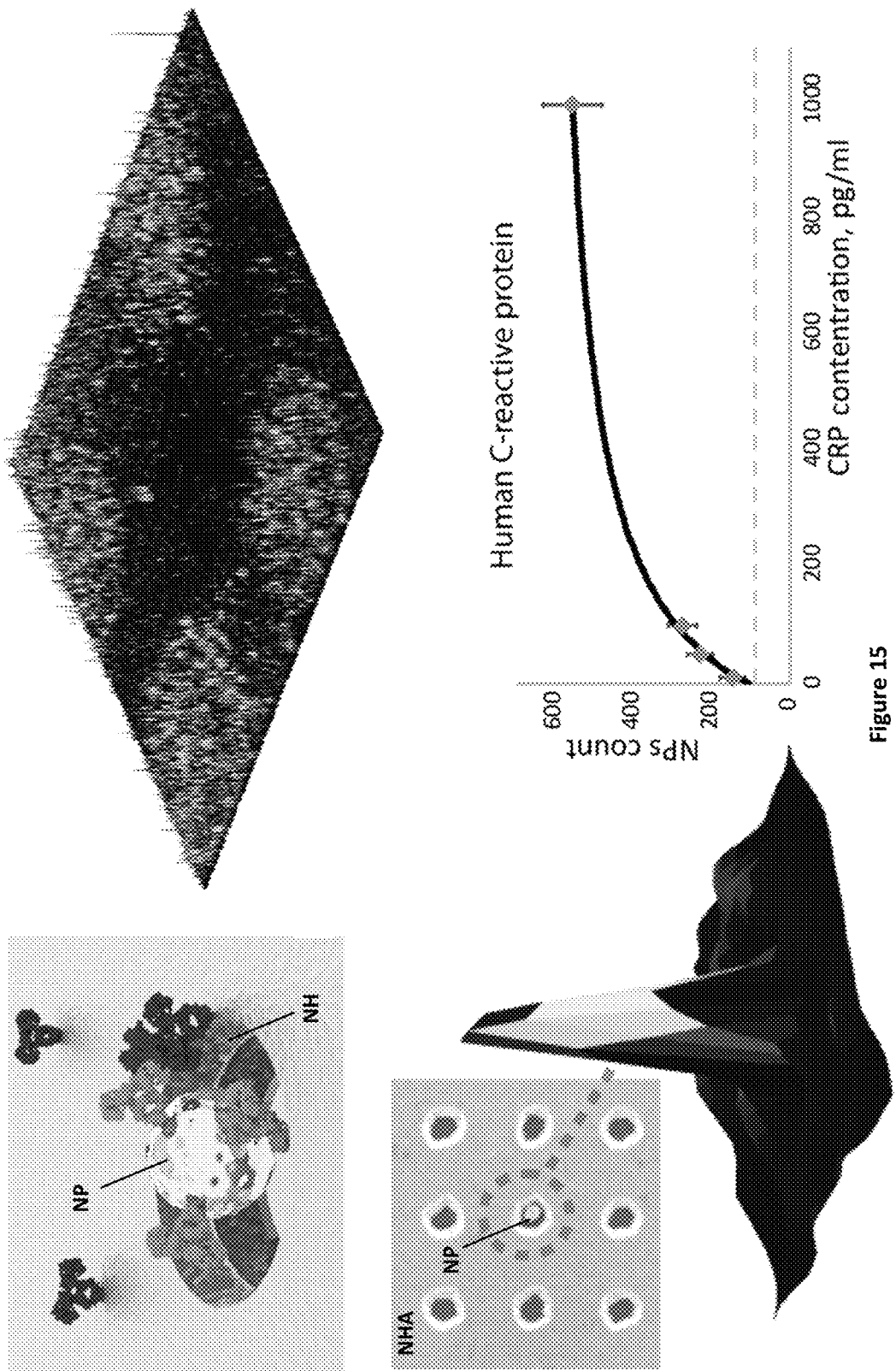

FIG. 15 shows aspects of a nanoparticle enhanced plasmonic imager according to the present disclosure.

Herein, identical reference numerals are used, where possible, to designate identical elements that are common to the Figures.

DETAILED DESCRIPTION OF SEVERAL EMBODIMENTS

FIGS. 1 to 5, 9 to 10 and 13 to 14 schematically show an exemplary plasmonic biosensor systems or devices 1 according to the present disclosure.

The plasmonic biosensor system 1 includes a nano-hole array device 3 comprising at least one nano-hole array NHA including a plurality of nano holes NH, the at least one nano-hole array NHA being able to be functionalized to capture a target antigen or biomarker, and at least one or a plurality of nano-particles NP configured to be received by the nano-holes NH of the nano-hole array NHA, the at least one or the plurality of nano-particles NP comprising or consisting solely of at least one metal and the at least one or the plurality of nano-particles NP being able to be functionalized with at least one molecule configured to bind or conjugate to a target antigen or biomarker.

The extraordinary optical transmission EOT in NHAs occurs through the hybridization of propagating surface plasmon polaritons (SPP) and localized surface plasmons (LSP) coupled to the nanoholes.[28] The propagating SPPs are excited by normally incident light through momentum matching by the periodic nanohole grid, due to a phenomenon known as Wood's anomaly.[44] This sub-radiant propagating mode is strongly damped through the radiation channels created by the strong field localizations at the nanoholes, leading to sharp Fano-shaped transmission peaks at the resonant wavelengths in the far-field spectrum (see FIG. 2I.). The transmission peak position is highly sensitive to the refractive index changes at the gold-medium interface and therefore can be used for the detection of molecular binding at the NHA surface.[45]

Contrary to the conventional detection approaches based on spectral peak shift monitoring [24-26,29-35], the transduction of the present disclosure concerns intensity changes of the EOT induced by the binding of functionalized nanoparticles. The plasmonic biosensor system or device 1 of the present disclosure exploits, for example, far-field intensity-imaging of the local EOT distortion induced by the binding of functionalized nanoparticles.

The plasmonic biosensor device or system 1 includes a nano-hole array device 3 comprising at least one nano-hole array NHA. The nano-hole array NHA includes a plurality of nano holes NH.

The system 1 can also include a light source A1 for illuminating the nano-hole array NHA, and an image sensor A3 for capturing light provided by the light source A1 and transmitted through the nano-hole array NHA.

The system 1 may also include at least one or a plurality of nano-particles NP. The nanoparticles are preferably configured to be received by and inside the nano-holes NH of the nano-hole array NHA.

The light source A1 may be broadband illumination source such as a white light source. Alternatively, the light source is a narrowband, for example, a LED. The FWHM emission wavelength range of the source may be, for example, 10 nm or less. The light source may be a polarized or non-polarized light source.

The light source A1 has a center wavelength and/or a FWHM narrow emission band matching or overlapping the plasmonic resonance of the nano-hole array NHA. The light source A1 may, for example, have a (substantially) 650 nm center wavelength, or a (substantially) 660 nm center wavelength and a (substantially) 10 nm FWHM narrowband.

A wavelength filer filtering a narrow wavelength band of the light emitted by the source A1 may also be included.

A light source having a center wavelength emission and/or a FWHM narrow emission band matching or overlapping the plasmonic resonance of the nano-hole array NHA is used for the intensity imaging. The center wavelength value preferably corresponds to the wavelength value at which a distortion in transmission occurs when a nanoparticle NP disturbs the EOT resonance or phenomenon generated in the nanohole array NHA.

The system 1 may also include a holder A15, for example an aluminum holder, configured to hold the nano-hole array device 3 and permit optical transmission measurements or images to be acquired. The holder A15 can, for example, define a chamber configured to receive the nano-hole array device 3 and/or the plurality of nanoparticles NP.

The system 1 may also include an objective lens A5 to collect light transmitted through the nano-hole array device 3 and to provide the collected light to the image sensor 3. The lens A5 may, for example, be a high magnification lens, for example, a 100× or 50× objective lens. A lens A7 may also be optionally included for collimating the light provided by the light source A1 onto the nano-hole array NHA.

The system 1 may also include other elements, for example, optical elements such as one or more beam splitters for directing the light or light beam; and/or one or more polarizers for controlling the polarization of the light illuminating the nano-hole array NHA.

The image sensor A3 may comprise or consist of, for example, a CMOS device or camera. The CMOS camera may comprise, for example, a plurality of pixels each configured to individually capture incoming light. The image sensor A3 may alternatively comprise an active pixel sensor (APS) containing an array of pixel sensors each comprising for example a photodetector and amplifier.

The system 1 may also include calculation means or a processor A10 connected to and configured to receive the captured image or image data from the image sensor A3. The calculation means or processor A10 may also be configured to control and command the image sensor A3. The calculation means or a processor A10 may also be connected to the other elements of the system 1 and configured to control and command these elements to permit operation of the system 1.

The system 1 may include a memory A12 (for example, semiconductor memory, HDD, or flash memory) configured to store or storing at least one program or processor executable instructions. The at least program or processor executable instructions may comprise instructions permitting, for example, to control and command the image sensor A3 and the other system elements. The processor executable instructions may comprise instructions permitting to receive and process the captured image or image data from the image sensor A3.

The calculation means or a processor A10 and the memory AU can be, for example, included in a computer, portable laptop or a portable device such a s a smart phone or device. The program or processor executable instructions can be provided, for example, as custom Matlab functions.

The processor executable instructions can include instructions permitting various different actions concerning capturing and processing images and image data of the present disclosure.

The processor executable instructions are provided or obtained by the processer for execution.

The nano-hole array NHA is configured to generate surface plasmons and to produce an extraordinary optical transmission EOT resonance.

An extraordinary optical transmission EOT resonance is a known phenomenon of enhanced transmission of light through a subwavelength aperture defined in an opaque layer or film, for example, a metallic layer or film which comprises, for example, a regularly repeating and/or a periodic plurality of such apertures.

The phenomenon is due to the presence of surface plasmon resonances and constructive interference. A surface plasmon is a collective excitation of electrons at a junction between a conductor and an insulator and provides an interaction with light resulting in EOT resonances.

An exemplary, nano-hole array device 3 and nano-hole array NHA is for example described in U.S. patent application US2017023476 (ALTUG et al), the contents of which are fully incorporated herein by reference.

The nano-hole array device 3 may include a substrate S1 supporting the nano-hole array NHA. The substrate can, for example, comprise or consist solely of glass or fused silica. An intermediate dielectric layer S2 may also be located between the substrate S1 and the nano-hole array NHA. The intermediate dielectric layer S2 may, for example, comprise or consist solely of silicon nitride.

The outer layer of the nano-hole array device 3 may comprise or consist solely of a metal or a noble metal. The outer layer may, for example, comprise or consist solely of gold (Au) or silver (Ag), or aluminium (Al), or copper (Cu), or titanium (Ti), or chromium (Cr).

The outer layer of the nano-hole array device 3 may comprise or consist solely of highly doped semiconductors including silicon, germanium, III-V semiconductors such as GaAs, III-nitrides such as GaN, transparent conducting oxides such as ITO, ZnO, perovskite oxides, metal nitrides, silicides, germanides, or 2D materials such as graphene.

The outer layer of the nano-hole array device 3 defines or delimits the nanoholes NH and the nano-hole array NHA. The nano-holes NH can be, for example, metallic nano-holes or noble metal nano-holes. The nano-holes may, for example, comprise or consist solely of gold (Au) or silver (Ag), or aluminium (Al), or copper (Cu), or titanium (Ti), or chromium (Cr).

The nano-holes can, for example, comprise or consist solely of highly doped semiconductors including silicon, germanium, III-V semiconductors such as GaAs, III-nitrides such as GaN, transparent conducting oxides such as ITO, ZnO, perovskite oxides, metal nitrides, silicides, germanides, or 2D materials such as graphene.

The nanohole NH may extend fully through the metal outer layer. The nanoholes, can for example be non-tapered or tapered outwards towards an external surface of the outer metal layer of nano-hole array device 3.

The nanohole NH is, for example, sub-wavelength in size or average diameter.

The average diameter of the nanoholes can have a value for example, between 100 nm and 300 nm, for example 200 nm. The average size or diameter can be measured, for example, using SEM.

The plurality of nanoholes NH may define or comprise, for example, a repeating symmetric pattern of nanoholes. A nanohole NH is, for example, periodically repeated. The distance between each nanohole NH may have a value P or the nanoholes NH may repeat periodically with the same period value P having a value, for example, between 200 nm and 800 nm, for example 600 nm.

The nano-holes NH can be, for example, configured or laid-out as a periodically repeating nano-hole array or arranged in a periodic array arrangement. The periodic arrangement may define a symmetric geometry.

The nano-hole arrangement may also be non-periodic. The arrangement may, for example, define a square lattice arrangement or hexagonal lattice arrangement.

The nano-holes NH may have a symmetric geometry, for example, substantially circular as shown in the Figures. The nano-holes NH may additionally or alternatively have other aperture shapes such as squares and/or co-axials.

The nanoholes can, for example, have a depth D that is at least equal to or less than: 0.25× the average diameter of the nanoparticle or 0.5× the average diameter of the nanoparticle or 0.75× the average diameter of the nanoparticle or 1× the average diameter of the nanoparticle or 1.2× the average diameter of the nanoparticle NP. The depth D is, for example, greater than 0.1× the average diameter of the nanoparticle NP.

The nano-hole array NHA may include one or more alignment marks permitting alignment and comparison of the acquired images and image data. The nano-hole array NHA may alternatively or additionally include one or more quick response QR codes permitting to encode information, for example, about components or elements of the biosensor.

The one or the plurality of nano-particles NP are, for example, sub-wavelength in size or average diameter.

The nano-particles NP can be, for example, (substantially) spherical nano-particles. However, the nano-particles may alternatively have other forms such as, for example, nanorods, nanostars or nanoshells. The nano-particles NP can have a (substantially) symmetric shape.

The nano-particles NP can have a size or an average diameter that is between 25% and 50% or 45% and 50% of the average diameter of the nano-hole NH measured at the external surface of the nano-hole array NPA, or between 25% and 55% or 45% and 55% of the average diameter of the nano-hole NH, or between 25% and 60% or 45% and 60% of the average diameter of the nano-hole NH, or between 25% and 100% or 45% and 100% of the average diameter of the nano-hole NH at an external surface of the nano-hole array (NPA).

The nano-particles NP are, for example, metallic nano-particles, or the nano-particles comprise or consist solely of one or more metals. The nano-particles can comprise or consist solely of a noble metal. The nano-particles may, for example, comprise a non-metallic or dielectric core enclosed or covered by a metallic shell. The nano-particles NP may comprise or consist solely of, for example, gold (Au), or silver (Ag), or platinum (Pt), or palladium (Pd), or cobalt (Co), or ruthenium (Ru), or rhodium (Rh), or osmium (Os), or iridium (Ir), or platinum (Pt), or rhenium(Re) or copper (Cu) or titanium(Ti), or niobium (Nb), or tantalum (Ta).

The nano-hole array NHA can be functionalized to capture a target antigen or biomarker. The nano-hole array NHA can be functionalized to capture a plurality of different target antigens or biomarkers. Different nano-hole arrays NHA may be functionalized to acquire different target antigens or biomarkers. The external surface around and/or between the nanoholes NH in the outer metal layer of nano-hole array device 3 can be functionalized. The inner wall or walls of the nanohole may also be functionalized.

The nano-particles NP can be functionalized with at least one molecule configured to bind or conjugate to this target antigen or biomarker. The capture or reception of the target antigen or biomarker by the nano-hole array and inside a nanohole or in proximity to a nanohole results in the nanoparticle NP disrupting the optical transmission of the nano-hole array NHA. Intensity changes of the EOT induced by the binding of functionalized nanoparticles NP occur. The plasmonic biosensor system 1 of the present disclosure exploits this by, for example, acquiring or measuring these changes via intensity-imaging of the local EOT distortion induced by the binding of functionalized nanoparticles.

Within proximity of the nano-hole NH can be defined, for example, as a distance from the external metallic perimeter of the nanohole NH, this distance being equal to or less than the average diameter of the nanoparticle NP, or 1.5 times the average diameter of the nanoparticle (NP). This distance can, be, for example, 100 nm or 150 nm.

A suppression or reduction of transmission intensity occurs and corresponds to a reduction in transmission intensity within a predefined spectral range of an extraordinary optical transmission (EOT) resonance.

The reduction in transmission intensity is, for example, a reduction of at least 5%, or at least 10%, or at least 20%, or at least 30%, or at least 40% of at least 50% of a reference transmission intensity obtained in the absence of nano-particles NP on the nano-hole array NHA.

The processor executable instructions contained in the memory A12 can comprise instructions permitting the calculation means or processor A10 to determine or count the nano-holes NH on the nano-hole array (NHA) at which a suppression or reduction of transmission intensity occurs using the received image or image data acquired by the image sensor A3.

The calculation means or processor A10 is, for example, configured to generate data or an image map identifying nano-holes NH on the nano-hole array NHA at which a suppression or reduction of transmission intensity occurs. The processor executable instructions comprise instructions to generate data or an image map identifying nano-holes NH on the nano-hole array NHA at which a suppression or reduction of transmission intensity occurs.

The calculation means or processor A10 can be configured to continually generate data or a plurality of image maps identifying nano-holes NH on the nano-hole array NHA at which a suppression or reduction of transmission intensity occurs and provide the data or image maps for display as a video permitting a real-time display or visualization of the running detection process. The processor executable instructions comprise instructions to continually generate data or a plurality of image maps identifying nano-holes NH on the nano-hole array NHA at which a suppression or reduction of transmission intensity occurs and to provide the data or image maps for display as a video permitting a real-time display or visualization of the running detection process.

The system 1 may include a display for visualizing the measured data and images.

The data or the image map is configured or arranged to provide a representation of the nano-particles NP inside a nano-hole (NH) or in proximity of the nano-hole NH of the nano-hole array NHA. The suppression or reduction of transmission intensity corresponds to the presence of a nano-particle NP in a nano-hole (NH) or in proximity of the nano-hole NH and corresponds to the detection of the target antigen or target biomarker.

The calculation means or processor A10 is configured to generate data or an image map by, for example, subtracting intensity values of a first image (or a part of the first image) acquired in the absence of nano-particles NP on the nano-hole array NHA from intensity values of a second image (or a corresponding part of the second image) acquired in the presence of functionalized nano-particles NP on the functionalized nano-hole array NPA. The processor executable instructions may comprise instructions to generate data or an image map by subtracting intensity values of a first image (or a part of the first image) acquired in the absence of nano-particles NP on the nano-hole array NHA from intensity values of a second image (or a corresponding part of the second image) acquired in the presence of functionalized nano-particles NP on the functionalized nano-hole array NPA.

The calculation means or processor A10 can also be configured to align the first image with the second image using the one or more alignment marks present in the first and second images. The processor executable instructions may comprise instructions to align the first image with the second image using the one or more alignment marks present in the first and second images.

The calculation means or processor A10 can also be configured to maximize the number of detected nanoparticles NP and minimizing the number of false positive by applying an intensity threshold to the generated data or image map. The processor executable instructions may comprise instructions to maximize the number of detected nanoparticles NP and minimizing the number of false positive by applying an intensity threshold to the generated data or image map The plasmonic biosensor system 1 of the present disclosure can be included in an optical reader or imager or a portable optical reader or imager.

The present disclose also concerns a plasmonic biosensing method. The nano-hole array device 3, the light source A1, the image sensor A3 and the plurality of nano-particles NP of the plasmonic biosensor system 1 are provided. Functionalizing of the nano-hole array (NHA) to capture a target antigen or biomarker is carried out, and functionalizing of the plurality of nano-particles NP with at least one molecule configured to bind or conjugate to the target antigen or biomarker is also carried out.

The plurality of functionalized nano-particles NP are mixed or brought into contact with the target antigen or target biomarker and then placed or dispersed on an external surface of the nano-hole array NHA.

Illumination of the external surface of the nano-hole array NHA with the light source A1 is carried out and at least one light intensity transmission image is acquired using the image sensor A3. Prior to placing or dispersing the plurality of functionalized nano-particles (NP) on the external surface of the nano-hole array NHA, at least one light intensity reference transmission image is captured or acquired.

The number of nanoparticles NP received by a nanohole NH of the nanohole array (NHA) and/or located in proximity to a nanohole NH is then determined. This can for example be carried out by subtracting the transmission intensity data of the transmission image (or a part of the transmission image) from the transmission intensity data of the reference transmission image (or a corresponding part of the reference transmission image) captured prior to placing or dispersing the plurality of nano-particles NP on the external surface of the nano-hole array NHA.

A number of specific but non-limiting exemplary embodiments of the method and system of the present disclosure are now presented.

To numerically investigate the local effects created by the Au-NP and the associated changes in the far-field spectrum of the Au-NHAs, the inventors used a commercially available finite-element frequency domain solver (CST microwave studio 2016). A unit-cell, composed of an exemplary 3×3 Au nanohole array (for example, diameter=200 nm period=600 nm) with periodic boundary conditions, is excited from top with normally incident TM mode (FIG. 3A). The size of the simulated 3×3 unit cell was chosen to match to the diffraction-limited spot (1.8 μm) resolved in the experimental imaging set-up.

When a 100 nm diameter gold nanoparticle NP binds to the inner walls or the vicinity of a nanohole rim, the localized dipolar resonance is disturbed. This local distortion in the resonant interactions leads to alterations in the radiation pathways and creates suppression of the EOT peak in the far-field (FIG. 3B). The Inventors explored the effect of the NP position on the resonance modes and found that when a NP binds to the top surface of the Au-NHA, its impact on the transmission depends on how close the NP is to the nanohole rim, where the hot-spots of localized hole modes reside. FIG. 3B shows that as the NP gets closer to the nanohole, the peak suppression increases, which correlates with the distortion of the localized enhanced fields presented in FIG. 3C. When a NP is on the gold surface far from the nanohole, it was observed that its effect on the NHA transmission is insignificant. This could be due to the spatially limited interaction of the propagating plasmon modes with the small NP volume. Whereas, a NP inside a nanohole produces a drastic or significant distortion on the localized modes, suppressing the transmission significantly.

Since the Au-NHAs have a symmetric geometry, their resonances are polarization independent and can be excited with unpolarised light. A NP trapped inside the nanohole can distort the dipolar modes in all lateral directions (see FIG. 6 for excitation polarization effect), resulting in a stronger suppression than the surface bound NPs close to the nanohole rim.

The Inventors also investigated the effects of NP size on the numerically computed far-field transmission spectra when Au-NPs of various diameters are entrapped inside a nanohole. FIG. 3D shows that the suppression of the transmission peak increases with the NP diameter and saturates at 100 nm. Moreover, it is important that experimentally the NPs can easily fit inside the nanoholes, both of which can have minor size variations. This defined a preferred choice in the experimental measurements of Au-NPs with 100 nm average size (±10% dispersity). The average size or diameter can be measured, for example, using scanning electron microscopy (SEM), or transmission electron microscopy (TEM), or dynamic light scattering (DLS). The average diameter of the nanoparticles can be, for example, determined using the equipment and/or methods set out as references 46 to 48, the contents of which are fully incorporated herein by reference.[46-48]

The Inventors also numerically investigated the effect of a dielectric $SiO_2$ NP with a 110 nm diameter and did not observe any amplitude change in the transmission peak of the Au-NHA, whether placed inside or outside of the nanohole (FIG. 7). These are expected outcomes as the local fields can penetrate through the dielectric media without being distorted, yet a minuscule or insignificant shift in the resonance wavelength is caused by the change in the effective refractive index of the top medium.

The strong local transmission quenching induced by the gold nanoparticle NP is procures the distinctive detection mechanism of the present disclosure. Numerical calculations indicate that individual particles can produce sufficiently strong spikes on the captured intensity contrast images from the plasmonic surface to be detected in a simple bright-field scheme.

For exemplary experimental demonstrations the Inventors used uniformly patterned Au-NHA (for example, diameter=200 nm, period=600 nm) sensor chips of, for example, area 1 $cm^2$. The plasmonic nanostructures uniformly covering entire 4-inch quartz wafers were fabricated using a robust high-throughput DUVL lithography[43] (FIG. 1D), yielding multiple low-cost sensor chips (50 chips/wafer), which is important for biosensing applications.

The Inventors post-patterned Au-NHA wafers to define 10×10 microarray regions on each chip by patterning labels using photolithography and metal (Ti) lift-off techniques (FIG. 1D). The size of each labelled microarray region is 800 μm×800 μm and each microarray region can be functionalized with 2×2 bioreceptor sensing spots (150 μm diameter spot), providing a flexible platform for multiplexed measurements.

The experiments are performed, for example, on an inverted microscope with a narrow-band illumination A1, centred at 650 nm with 10 nm full width at half maximum (FWHM), Illumination is at the wavelength at which the exemplary Au NHA with 600 nm period and 200 nm diameter have a resonant transmission peak, where the images are recorded at 1 second exposure on a 1608×1608 pixels grayscale CMOS camera A3. The optical path is configured to reach 30× total magnification using a 0.3 numerical aperture (NA) objective lens A5 and a 0.13 NA condenser A7. This optical arrangement enables the capture of images covering a 385×385 $μm^2$ area, with a Rayleigh diffraction-limited spot size of $$R = 1.22 \frac{\lambda_{illumination}}{NA_{condenser} + NA_{objective}} \sim 1.8 \text{ μm},$$

Note that this diffraction-limited area corresponds to a 3×3 nanohole unit cell, which is considered in the numerical analysis above. A detailed description of the optical set-up can be found below. To accurately extract the positions of NPs from the imaging data, images of bare Au-NHA chips patterned with non-transparent (Ti) alignment marks prior to the bioassay (FIG. 4A) are acquired. This is useful because the transmission of bare Au-NHAs exhibits minor spatial intensity variations, independent of the imaging set-up. This could be attributed to several reasons, such as minor differences in the metal film crystal structure or the nanohole uniformity. In order to account for these minor intensity variations, referencing of the images of Au-NHA sensors before and after the bioassay with NPs can be carried out.

Next, one performs the sandwich bioassay by first functionalizing the Au-NHA chips using a non-contact micro-dispenser with 2D arrays of capture molecules through gold-thiol surface chemistry. Then, the chips are successively incubated with the analyte dilutions and a suspension of Au-NPs conjugated to receptor molecules (See below for further details). After the sandwich assay, the Au-NHA chips are rinsed, dried and imaged again (FIG. 4B). The images (for example, intensity images at one wavelength, for example, the resonant transmission peak wavelength) of the corresponding microarray regions before and after capturing the target analyte and NPs are aligned and subtracted using, for example, a custom-made Matlab function or processing of the data of the captured images. The two images can be first matched, for example, by referencing to identical microarray alignment marks, then, for example, scaled to the same average intensity range, corrected for background illumination gradients, then subtracted and, for example, normalized.

The alignment and subtraction of the images before and after yield highly accurate intensity maps or heatmaps of NPs binding on Au-NHAs, represented as local intensity spikes (FIG. 4C). Finally, the NPs are automatically identified and quantified from the spikes on the map or plasmonic heatmap using a fixed-value threshold. The optimal threshold depends on the imaging characteristics of the optical set-up, and was empirically found to be 5% intensity change in the microscope system by mapping plasmonic images to high-resolution Scanning Electron Micrographs (SEM) for NP verification. The optimal threshold value is for example chosen to detect the maximum number of nanoparticles, while keeping a low rate of false positive signals.

To quantitatively analyze the accuracy of the NP enhanced plasmonic imaging technique, plasmonic images were matched to the SEMs of the microarray elements. FIG. 4D shows two representative plasmonic heatmap parts and their corresponding SEM from NPs deposited microspots (I) and NP-free regions (II). The details on the test sample preparation used for the system characterization are provided further below.

In agreement with the simulations, most of the detected NPs are bound inside the nanoholes, which are marked with dark circles on the SEMs in FIG. 4D (also shown in FIG. 4E-1). Intensity peaks, recognised as NPs, are highlighted by arrows on the plasmonic images. A small fraction of NPs outside of nanoholes, close to the edges of the holes, could also be detected, supporting our numerical results regarding NP-NHA interactions through disruption of localized nanohole modes (FIG. 4E-3). As expected, the NPs that are bound far from the nanoholes were not detected (FIG. çE-2). After mapping over 1000 NPs on numerous SEM images, we found that 40% of NPs bind inside nanoholes and 60% over the gold surface as summarized in FIG. çF. From the plasmonic heatmaps, one is able to detect approximately 40% of all nanoparticles, with a 3% false positive signal rate based on data with a sample size of 127 plasmonic intensity peaks matched to SEM. In addition, this detection is robust against non-specifically binding agglomerates of NPs and large sedimenting contaminants, since they can be easily identified and discarded by the size and the shape of intensity spikes on the plasmonic imaging surface.

It is first shown the biosensing potential of the NP-enhanced plasmonic imaging method and system of the present disclosure in a proof-of-principle detection of biotinylated BSA bBSA as depicted in FIG. 5A. Reference images are first acquired on the chips that will be used for the bioassays. Next, the Au-NHAs were surface functionalized with PEG-thiol chemistry to prevent non-specific fouling and ensure optimal protein immobilization through EDC-NHS crosslinker. Then, microarrays of neutravidin (150 pl droplets spotted with 200 µm pitch) were formed using a non-contact micro-dispenser and the remaining areas were blocked with BSA to deactivate non-reacted cross-linker groups. The bBSA dilutions were spiked in 100 µl PBS 1× and incubated with the Au-NHA chips. Finally, a suspension of Au-NPs covalently tethered to streptavidin in PBS 1× with 1% BSA was incubated. After rinsing with milliQ water and drying under N2 stream, the second set of images was acquired. Further details on the bioassay procedure are given further below. To quantify bBSA, the image datasets were processed as described above. The local intensity spikes were counted over $100\times100$ µm$^2$ neutravidin spotted areas (see FIG. 5B), and the results are correlated to the bBSA concentrations (FIG. 5C). It is experimentally shown the successful detection of bBSA concentrations down to 10 pg/ml, which is equal to the Inventors estimated limit-of-detection (LOD, computed by adding three times the standard deviation of control signal to the average of the control). These results show that the method and system of the present disclosure reaches the sensitivity of fluorescence amplification techniques, while avoiding the signal amplification step, such as used in typical ELISA. To put into context, a concentration of 10 pg/ml of bBSA translates to $9\times10^6$ molecules in a 100 µl sample incubated on a sensor chip ($1\times1$ cm$^2$). The ratio of a single sensing spot ($100\times100$ µm$^2$) to the entire sensor chip ($1\times1$ cm$^2$), is roughly $1:10^4$, which, accounting for molecular diffusion limitation, results in a few hundred molecules reaching to a single sensing spot of $100\times100$ µm$^2$. Taking into account the diffusion limitation of nanoparticle tags and that 40% of bound particles can be detected binding inside or close to the nanoholes, the 10 pg/ml concentration would result in approximately ~10-100 NPs counts. This estimation is in agreement with the assay, where the 10 pg/ml LOD produced on average 50 nanoparticle counts per read-out spot. The above results indicate that the detection method and system ultimately operates near the actual diffusion limitation of the system. In this way, the extraction of intensity spikes from the plasmonic imaging heatmap allows to digitally count the analytes with high sensitivity, contrary to conventional affinity sensors where the signals are averaged over sensor areas.

The flexibility of the developed method and system of the present disclosure enables its use in a variety of bioanalytical applications, by using appropriate biofunctionalization procedures. In order to show the diagnostics potential of the platform, human C-reactive protein (CRP) is detected. Human CRP is a blood biomarker, whose levels elevate during acute inflammatory conditions, such as sepsis and coronary heart disease. Septic shock is caused by the response of body to infections and is one of the most pressing healthcare challenges worldwide with millions of patients diagnosed each year and over 20% of lethal incidence.[49] Therefore, the development of biosensors enabling timely and accurate detection of biomarkers such as CRP can have a profound impact on the effective disease management.

The method and system of the present disclosure are used in a single-step sandwich immunoassay to detect human CRP from bovine serum albumin (BSA) solution. FIG. 5D illustrates the CRP detection and the details of the assay can be found further below. The Inventors experimentally detect CRP concentrations down to 27 pg/ml, which is four orders of magnitude within clinically critical limits, thus opening the path for early-stage disease monitoring. As expected, the LOD for CRP is slightly higher than 10 pg/ml LOD in bBSA detection (FIG. 5 E,F), since the CRP assay was performed in media with high BSA concentration, which may screen antibody-antigen interactions. Additionally, the affinity between anti-CRP antibodies and CRP are normally lower than affinity between biotin and streptavin or neutravidin.

FIGS. 5C and 5F presents the calibration curves of bBSA and CRP measurements. The non-specific nanoparticle adsorption, indicated with dashed grey lines, was the main limitation for the LOD in both assays. The control experiments were performed by incubating chips in samples containing no analyte (i.e. bBSA or CRP), while all other assay steps remained unchanged. In CRP measurements, the NP concentration was higher than in bBSA assay, which was reflected on higher specific NP counts, but also higher baseline signal from non-specific NP adsorption. Importantly, the current results are well comparable to the high performance of commercial ELISA kits, which can detect down 3-15 pg/ml of human CRP when performed in a fully equipped clinical laboratories by trained personnel.[42]

Moreover, the present method and system can be used in real-time measurements in aqueous environment as well (image in FIG. 8 shows NPs binded to NHA in-flow), because the localized field disruption of Au-NHAs by Au-NPs is highly surface-confined and is also valid for the plasmonic resonances in wet medium.

Further applications with serum or whole blood-samples, as well as multiplexed biomarker detection are also possible with this approach.

A simple device or optical reader may include a narrow-band illumination source, an optical path sufficient for 1-2 µm spatial resolution and a CMOS sensor in conjunction with image processing algorithms and possibly a processor or calculator, and permit on-site diagnostic applications.

The present disclosure thus concerns a NP-enhanced imaging-based plasmonic biosensing technique or system using large-area NHA sensors. By disrupting localized plasmon modes in a NHA surface with NPs, the method produces plasmonic heatmaps that visualize single sub-wavelength NPs under bright-field imaging. Consequently, by detecting individual NP-labeled molecules one can digitally quantify the single analyte binding events on the imaging surface, enabling multiplexed detection of biomarkers at low concentrations, eminently at the level of current gold-standard laboratory methods, such as ELISA. At the same time, the technique and system avoids multi-step staining procedures and does not rely on advanced read-out set-ups, such as required in fluorescent techniques. The proposed method and system was used in sandwich immunoassay measurements of bBSA and human CRP, achieving clinically relevant detection limits of 10 and 27 pg/ml, respectively. Prominently, the large-area NHA sensor chips are fabricated in a large-scale low-cost manufacturing, giving versatility for high-throughput biosensing applications. Overall, the simple and scalable detection approach paired with robust sensor chips provides a flexible platform for highly sensitive multiplexed measurements in various settings, including for point-of-care applications.

In an exemplary embodiment of the present disclosure, gold nanohole arrays are fabricated and used. Gold nanohole arrays (Au-NHAs) were fabricated using high-throughput wafer-scale deep-UV lithography (DUVL) and ion beam etching techniques. First, 4-inch fused silica wafers were cleaned with RCA solution (1:1:5 $H_2O_2$:$NH_4OH$:$H_2O$), rinsed with deionized water and dried under nitrogen stream. Cleaned wafers were coated with 10 nm of titanium (Ti) and 120 nm of gold (Au) in Alliance-Concept EVA 760 electron-gun evaporator. The NHAs of 600 nm period and 200 nm diameter were patterned using a 248 nm deep-UV stepper (ASML PAS 5500/300 DUV). The nanohole arrays were transferred into metal films with ion-beam etching (Oxford Instruments PlasmaLab 300 IBE) and the photoresist was stripped with oxygen plasma.

Microarray marks on Au-NHAs were formed with Ti to enable image recognition and alignment. The NHA wafers were coated with 1.3 µm AZ1512 positive photoresist and microarray patterns were exposed using Heidelberg MLA150 laser writer. After resist development, 50 nm Ti was evaporated using an electron gun evaporator. Next, the wafers were diced into 1×1 $cm^2$ chips. The resist was removed from chips by immersing in resist remover with sonication at 70° C. for 2 hours. Finally, the chips were cleaned in oxygen plasma for 5 min at 500 W and RCA solution (1:1:5 $H_2O_2$:$NH_4OH$:$H_2O$ by volume) for 1 min to ensure uniformly clean gold surface.

To numerically investigate the local field effects on Au-NHAs created by the Au-NPs and the associated changes in the far-field spectrum, the inventors used a commercially available finite-element frequency domain (FEFD) solver (CST microwave studio 2016, Materials and Methods Section). The Inventors simulated Au-NHAs of 200 nm diameter and 600 nm period in an Au/Ti (120 nm/10 nm) thin film (optical parameters from Johnson and Christy) on a 500 nm thick $SiO_2$ substrate with refractive index (RI)=1.46 and air background media (RI=1). The Ti layer not only serves for Au adhesion to the silica substrate in fabrication, but also suppresses undesired gold-substrate modes, ensuring sharp shape and good isolation of plasmonic resonant modes in Au-NHA transmission.[33,50] The simulated unit cell contains 3×3 nanoholes with periodic boundary conditions. The unit cell size was chosen to correspond to the about 1.8 µm diffraction limited spot resolved in the experiments. The illumination is set from top with normally incident TM mode. The electric field was monitored at 650 nm (461 THz).

Concerning the optical set-up used for optical measurements, the microscope measurements were performed on an inverted Nikon Eclipse Ti-E system. A tungsten halogen lamp was used for illumination together with a narrow-band optical filter (Thorlabs) with 650 nm center wavelength and 10 nm full width at half maximum, matching the plasmonic resonance of Au-NHAs in dry. Optical path included a 20× and 0.3 NA objective lens and a 1.5× intermediate microscope magnification. Images were recorded using a Nikon Qi2 camera with 1 sec exposure and 1.2 digital gain.

For the bBSA and CRP measurements, ammonium hydroxide solution (ACS reagent, 28-30%), hydrogen peroxide (H2O2 30%), N-hydroxysulfosuccinimide sodium salt (sulfo-NHS), N-(3-dimethylamino propyl)-N'-ethylcarbodiimide hydrochloride (EDC), 2-(N-Morpholino)ethanesulfonic acid (MES), bovine serum albumin (BSA) lyophilized, biotinylated BSA (bBSA), neutravidin, phosphate buffered saline (PBS) and Tween® 20 were purchased from Sigma-Aldrich. Ethanol (EtOH), absolute was from Thermo Chemicals. Polyethylene-glycol (PEG) thiols terminated with hydroxyl (HS-C6-(EG)4-OH) and carboxyl (HS-C11-(EG)4-OCH2-COOH) groups, were purchased from Prochimia. Human C-reactive protein (CRP) and anti-CRP monoclonal IgG antibodies PCR-196 and PCR-183, used as capture and recognition antibodies respectively, were provided by Diesse Diagnostica Senese. Spherical gold nanoparticles of 100 nm dimeter coated with streptavidin or with protein-G, supplied at optical density (OD) 3 in PBS with 20% glycerol and 1% BSA, were purchased from Cytodiagnostics (A 100 nm diameter gold nanoparticles concentration of optical density (OD) 1 corresponds to 5.6E9 nanoparticles per 1 ml solution; the relation between OD and NP/ml units is linear).

Au-NHA functionalization can be carried out as follows. After cleaning in oxygen plasma and RCA, Au-NHA chips were immersed and incubated overnight in 1 mM PEG-thiol solution in anhydrous ethanol with OH:COOH terminated PEG mixed in 5:1 ratio. After incubation, chips were gently rinsed with fresh ethanol and milliQ water, then dried under N2 stream. The chips were activated in 70 mg/ml EDC and 20 mg/ml s-NHS mixture in 0.1 M MES buffer for 20 minutes. Next, the chips were rinsed in milliQ water and dried under N2 stream. Monoclonal anti-CRP IgG196 or neutravidin were immediately spotted on the activated Au-NHAs using Scienion S3 piezoelectric non-contact microdispenser. The spotting solution contained either neutravidin or anti-CRP IgG at 200 µg/ml in PBS 1× with 0.5% glycerol. The average droplet volume was 160 pl and the contact area of the formed spot was approximately 100 µm in diameter. The spotted chips were incubated overnight in a humid atmosphere at 4° C. and then blocked with BSA 1% solution in PBS to passivate the non-reacted EDC-activated groups. Functionalized chips were used in measurements on the same day.

Biotin-BSA sandwich assay: Au-NHA chips spotted with neutravidin and blocked with BSA were briefly rinsed in PBS and immersed in 100 µl of biotin-BSA calibration dilutions prepared in PBS 1× and incubated for 1 hour. Next, each chip was rinsed in PBS 1× with BSA 1% and 0.05% Tween 20 for 20 minutes. After a brief immersion in PBS 1× with BSA 1%, the chips were incubated for 1 hour in Streptavidin-conjugated gold nanoparticles diluted to OD 0.1 in PBS 1× BSA 1%. After incubation, the chips were rinsed in milliQ water for 5 mins and dried under gentle $N_2$ stream.

Au nanoparticle conjugation to anti-CRP antibodies: 40 µl of 100 nm gold nanoparticles conjugated to protein G at OD 3 concentration were mixed with 1 µl of 2.1 mg/ml anti-CRP PCR183 antibody by gentle pipetting and incubated overnight at 4° C. Next day, the nanoparticle-antibody solution was diluted in 1 ml of PBS with 1% BSA and centrifuged at 200 g until a nice pellet was formed. After removing the supernatant, the pellet was resuspended in 1 ml of PBS 1× with 1% BSA. Centrifugation and resuspension steps were performed 4 times to remove unbound antibodies from NPs suspension. After the final centrifugation and supernatant removal, the NPs were resuspended in 40 µl of PBS 1× with 1% BSA. The conjugated nanoparticles were used for measurements on the same day.

CRP sandwich assay: Au-NHA chips spotted with anti-CRP IgG 196 and blocked with BSA were briefly rinsed in PBS and immersed in 100 µl of CRP calibration dilutions prepared by spiking CRP in PBS 1× with 1% BSA. After 1 hour incubation, chips were rinsed in PBS 1× with BSA 1% and 0.05% Tween for 20 min with gentle agitation on a gyro-rocker. After brief immersion in PBS 1× with BSA 1%, the chips were incubated for 1 hour in IgG183-coated Au-NPs diluted to OD 0.2 in PBS 1× BSA 1%. After incubation, chips were rinsed in milliQ water for 5 min and dried under gentle $N_2$ stream.

While the invention has been disclosed with reference to certain preferred embodiments, numerous modifications, alterations, and changes to the described embodiments, and equivalents thereof, are possible without departing from the sphere and scope of the invention. The features of any one of the described embodiments may be included in any other of the described embodiments. The methods steps are not necessary carried out in the exact order presented above and can be carried out in a different order. Accordingly, it is intended that the invention not be limited to the described embodiments, and be given the broadest reasonable interpretation in accordance with the language of the appended claims. Accordingly, it is intended that the invention not be limited to the described embodiments, and be given the broadest reasonable interpretation in accordance with the language of the appended claims.

The system 1 and method of the present disclosure was also used to show that the system 1 provides a portable plasmonic imager for rapid clinical biomarker detection, in particular rapid sepsis biomarker detection.

The device or system 1 was deployed at Vall d'Hebron University Hospital in Spain, and tested for the detection of PCT and CRP from serum of patients with sepsis, SIRS, and healthy individuals. The Inventors directly compare the results against ultimate clinical diagnosis and currently used immunoassay tests, and show that the system 1 enabled accurate classification between the three groups. Importantly, the testing is performed in a simple single step assay, and the detection of septic and SIRS patients can be achieved in 5 and 10 minutes, respectively. The compactness and cost-effectiveness of the device or system 1 make provide a rapid and accurate tool for on-site sepsis diagnosis.

A new clinical trend in sepsis management relies on blood testing to monitor patient's systemic response for rapid patient stratification. These tests which quantify circulating biomarkers, such as procalcitonin (PCT) and C-reactive protein (CRP) can not only help diagnose sepsis timely and reduce over-prescription of antibiotics, but also provide invaluable quantitative information to triage patients based on their anomalous response allowing for its personalized treatment. The current gold standard clinical tools to test blood circulating proteins are largely based on complex and lengthy immunoassays, such as enzyme linked immunosorbent, immunoturbidimetric and chemiluminescent assays, which require fully equipped clinical laboratories. However, having rapid access to the patient's systemic response, using portable, low-cost, and easy-to-use devices that can rapidly detect biomarkers in a simple manner from small sample volumes can drastically improve sepsis care at different clinical settings such as emergency departments, primary care settings and outpatient health centers.

The system 1 of the present disclosure provides a portable digital nanoparticle-enhanced nanoplasmonic imager for sepsis diagnosis (DENIS). DENIS enables rapid, sensitive and cost-effective detection of blood-circulating biomarkers directly in patient samples. The unique nanoplasmonic detection mechanism is based on gold nanoparticle (Au-NP) binding to plasmonic gold nanohole array (Au-NHA), which enables quantification of individual molecule binding on the sensor surface in complex media. The bioassay is performed in a single step without signal amplification or washing procedures, and the plasmonic detection is robust against variations in optical properties of samples. Importantly, the imager is made of off-the-shelf optical components, and its small size enables deployment and operation in on-site clinical settings.

Moreover, the sensor chips are produced in a scalable cost-effective manufacturing and the bioassay reagents can be stored in the fridge stably over weeks. The application of DENIS is shown for highly sensitive, quantitative and robust detection of two biomarkers used to diagnose sepsis, PCT and CRP. The system enables ultra-high detection sensitivities and a wide dynamic range with limit-of-detection (LOD) down to 21 pg/mL and 36 pg/mL for PCT and CRP, respectively, and dynamic range of at least 3 orders of magnitude. These values are well compatible with the reported ranges of these biomarkers used for clinical diagnosis. The diagnostic performance of DENIS is evaluated in clinical settings by testing the samples from sepsis, SIRS and healthy subjects provided by Vall d'Hebron Sepsis Bank. The quantitative detection of PCT and CRP from blood serum enabled the discrimination of healthy and sick groups with 100% accuracy based on 25 patients. Moreover, the PCT detection results show high predictive values for classification between SIRS and sepsis patients with 100% sensitivity and 87.5% specificity. Finally, DENIS can perform rapid detection by recording video of the plasmonic sensor and analysing the signals in real time. The time-resolved results revealed that sepsis can be identified and SIRS in 5 and 10 mins, respectively, reducing the total time-to-result to 15 mins. Detection mechanism: The DENIS detection mechanism is based on a large-area plasmonic Au-NHA (200 nm diameter, 600 nm period) device exhibiting extraordinary optical transmission (EOT) at its resonance wavelength when illuminated in a collinear optical path. This plasmonic resonance is locally distorted upon the binding of single Au-NPs (100 nm diameter). These distortions result in local suppression in the EOT, which enables detection of single NP-labelled molecules. Although the NPs are subwavelength in size, their plasmonic interaction with the Au-NHA allows for high-contrast imaging of surface-bound NPs in a simple bright field optical reader over large field of view directly inside complex samples. The imaged data is not affected by the bulk sample background because the resonance transmission through Au-NHAs is strictly dependent on the surface localized field with [18] 100 nm decay length. Moreover, the contrast generated by a single particle is significantly above the noise level induced by the camera and the sample, therefore individual molecules binding can be robustly quantified in a digital way directly in complex media. Importantly, single NPs can be distinguished on plasmonic images from NPs aggregates and sediment by the size and the shape of the plasmonic image spikes.

Plasmonic microarray sensors: the method and system 1 is used to quantify PCT and CRP biomarkers from human serum samples. In the presence of the biomarker in the sample, antibody-conjugated Au-NPs bind to the Au-NHA surface functionalized with complementary antibodies (FIG. 9a) and can be detected using a portable reader (FIG. 9b). Individual Au-NPs bound inside or close to the nanoholes (FIG. 9c) create strong local intensity contrast (FIG. 9d), which corresponds to digital detection of single analyte molecules.

To enable microarray based multiplexed biosensing, capture antibodies are bioprinted on the sensor surface using a high-throughput, non-contact, low-volume liquid dispenser as shown in FIG. 9e. The Au-NHA sensors are manufactured using a low-cost wafer-scale deep UV lithography and ion beam etching (FIG. 9f). The nanofabrication process enables production of over 50 highly uniformly nanostructured chips (1 cm×1 cm) per 4-inch wafer and 8 wafers per batch with negligible variation in optical properties. This robustness in the manufacturing of nanostructured sensors is critical to enable the transfer of the technology to a clinical diagnostic tool. Post-patterning the fabricated chips was done with an array of Quick Response (QR) codes (FIG. 9g). In addition to tagging individual chips and microarray locations on the chips, QR codes encode the information about the fabrication batch parameters and the wafer enabling a registry record of the manufactured sensors.

Optical reader: The nanoplasmonic imager 1 is made of off-the-shelf optical components and comprises a narrow-band light emitting diode (LED) source, a custom-built aluminium holder for the nanoplasmonic chip, an objective and a CMOS camera. The collimated LED light is transmitted through the sample chamber and modulated by the Au-NHA sensor. The sensor images are acquired by a 50× objective and CMOS sensor with 4104×3006 pixels and 3.45 µm pixel size. Each image shows a 900 µm×700 µm field of view (FOV) with about 1.2 µm resolution (FIG. 9g). The reader weight is below 1 kg and the dimensions are 10×10×35 cm. Such compactness means it is easily transportable and can be deployed in most on-site settings.

The control of the camera, image acquisition, and data processing are performed on a portable laptop PC using custom Matlab functions. Images are recorded with custom auto-exposure to ensure optimal intensity profile, corrected for source illumination, and the NPs binding is quantified over the sensing spots by computing the percentage of dark pixels using a cut-off threshold. QR tags from the images can be automatically recognized by custom Matlab function to register individual FOVs. For end-point measurements, signals from at least five microarray areas from each sensor chip are recorder for statistical significance. In the case of time-resolved measurements, images of a single FOV are recorded with 30 sec intervals, and the signals are extracted from at least three microarray spots to estimate mean and standard deviation. In order to control for non-specific NPs binding and background fluctuations, in each measurement the signals from BSA blocked background can be subtracted from the signals of Ab microarray spots.

Bioassay: The simple and rapid bioassay is performed in a single-step, where antibody functionalized Au-NP (Ab-NP) suspension is mixed directly with blood serum and then injected into the measurement chamber (FIG. 10a). Large batches of Ab-NPs are prepared with optical density OD=20 and stored in Phosphate Buffer Saline (PBS 1×) buffer with Bovine Serum Albumin (1% w/v) and Tween20 (0.05% w/v). The Ab-NP suspension is stable at 4° C. for at least 5 weeks, over which the tests were performed. The sensor chips are first uniformly functionalized with copoly-DMA-MAPS-NAS-fluorinated polymer (MCP-2F) to ensure stable antibody immobilization, prevent non-specific NP binding, and fouling by serum proteins. To form antibody microarrays, we spot antibodies specific to the biomarkers as well as mouse isotype immunoglobulin-G (IgG) for non-specific negative control both at 200 µg/mL. Each microarray spot of about 150 µm diameter, is formed by a single 400 pL droplet dispensed with 400 µm period. Importantly, the use of microarray printer not only enables functionalization of large number of chips, but also minimizes the amount of antibodies used, which are one of the most expensive components of the assay. The uniform antibody immobilization on the sensor surface is ensured by adding trehalose (0.5% w/v) and Tween20 (0.01% w/v) in the PBS 1× spotting buffer. The sensor chips with IgG microarrays are blocked with BSA (1% w/v) to minimize the non-specific binding. A capillarity-based disposable microfluidic platform is sealed on the sensor chips using a silicone spacer. The antibody immobilized chips can be stored at 4° C. stably for at least 5 weeks. To increase the performance of our assay, a stabilizing buffer was optimized, which consists of PBST (1×, 0.05% w/v) and NaOH (50 mM) in 3:1 ratio. To perform the bioassay, 20 µL of serum is mixed with 4 µL of Ab-NP suspension and 16 µL of stabilizing buffer, and the mixture is loaded into the measurement chamber with a pipet. The loaded cartridge is either inserted into the reader for time-resolved data acquisition or measured after an incubation period.

To characterize the performance of DENIS system, calibration titration curves were obtained by spiking known amounts of PCT and CRP biomarkers in reference samples (FIG. 10b,10c). Each data point represents mean value and standard deviation from five measurements collected from different microarray areas. The LOD values were estimated by measuring the mean signal from blank samples and adding three times the standard deviation. The detection method and system 1 achieves LOD of 21 pg/mL and 36 pg/mL for PCT and CRP, respectively. Moreover, the PCT dynamic range is three orders of magnitude (i.e. from about 21 to >1E4 pg/mL) covering the relevant diagnostic values. The clinical serum levels for CRP range from few μg/ml for healthy individuals to hundreds μg/mL for septic patients, which are significantly higher than the values for PCT. To measure them with the same assay, we diluted serum for CRP measurements in order to comply with the dynamic range of the device, which covers from 36 to 1E5 pg/mL. Importantly, the sensitivity and dynamic range enabled by the DENIS are similar to the performance of gold standard lab techniques, such as CLIA, without the need for time consuming amplification and washing steps or bulky readout equipment.

Clinical tests of the DENIS system: the DENIS system 1 was deployed at the Vall d'Hebron University Hospital and tested with clinical samples previously collected from patients with sepsis or SIRS and healthy individuals (previous informed consent agreement). Samples and data from the patients used in this study were provided by the Sepsis Bank of Vall d'Hebron University Hospital Biobank (PT17/0015/0047), integrated in the Spanish National Biobanks Network. Samples were processed following standard operating procedures with the appropriate approval of the Clinical Research Ethics Committee (approval reference number PR(AG)11/2016). It was obtained and measured on the DENIS platform samples, previously anonymized, from 25 individuals, including 12 patients with sepsis, 8 with non-infectious SIRS, and 5 healthy donors. The detection of PCT and CRP levels in the patients serum was performed as described above using only 20 μl of sample for each measurement.

In order to eliminate bias, the measurements were done in a blind manner, where neither the patient status nor the biomarker levels were disclosed during the testing. After completion of the clinical tests, the results collected from DENIS assay were compared with the routine clinical determinations.

Specifically, CRP and PCT detection were performed using immunoturbidimetric assay (ITA) and chemiluminiscent immunoassay (CLIA), respectively, and bacterial infection was determined with blood culture. The example images of single PCT spots obtained by DENIS system directly in serum from the three patient groups are presented in FIG. 10d. Samples from septic patients contain high levels of PCT and CRP, and result in dense binding of particles on antibody microspots of the Au-NHA sensor, while SIRS samples produce images with sparsely bound NPs, and healthy samples present negligible NP binding on the sensing areas. FIG. 10e shows CRP and PCT values measured from nine representative individuals from the three groups. Each data point represents the mean and STD from at least 5 different spots. Consistent results were observed correlating the PCT readouts from DENIS to the CLIA measurements in the clinical lab (inset FIG. 10e). In every sample measured, we controlled for non-specific interactions between Ab-NPs and the Au-NHA surface by recording signals from mouse IgG spots and BSA blocked areas.

Notably, we observed no significant signals from these control measurements on every chip tested. To validate the diagnostic performance of the DENIS platform, the PCT and CRP results of 25 individuals based on their clinical diagnosis were mapped (see FIG. 11a,11b). The measured levels of both PCT and CRP were significantly higher in SIRS patients than in healthy individuals ($P_{PCT}<1.4E-4$ and $P_{CRP}<1.3E-3$, unpaired t-test). Sepsis group presented higher serum levels of PCT and CRP compared to SIRS, however the difference in CRP levels was less significant ($P_{PC}<2.5E-5$, $P_{CRP}<4.15E-2$, unpaired t-test). Moreover, receiver operating characteristic (ROC) curves were constructed using the measured PCT or CRP values as a predictor and calculated the corresponding area under the curve (AUC) (FIG. 11c,11d). ROC curves are an established metric to analyse diagnostic ability of a test to discriminate the true state of subjects, and to compare two alternative diagnostic tests when each is performed on the same subject. Both biomarkers provided 100% sensitivity and specificity in classifying between healthy and sick groups. However, we observed that PCT is a better indicator of host response to infection in sepsis compared to CRP, with PCT AUC=0.99 and CRP AUC=0.71. Using PCT as a predictor provided a better classification between sepsis and non-infectious SIRS with Sensitivity=1 and Specificity=0.875, compared with CRP Sensitivity=0.92 and Specificity=0.625. The results obtained with clinically-validated immunoassays similarly showed better diagnostic performance of PCT compared to CRP. These findings are in agreement with the literature, where PCT levels in blood were shown to be more useful than CRP levels in discriminating SIRS from sepsis patients. To further evaluate the diagnostic performance the results were correlated with the clinical scores of the patients. These scores including Sequential [Sepsis-related] Organ Failure Assessment (SOFA) and Acute Physiology, Age, Chronic Health Evaluation II (APACHE II) are computed from a multitude of physiological parameters and are used to assess organ dysfunction and risk of death. It was found that the correlation between these scores and the PCT results are similar for both DENIS and current immunoassays. Importantly, the results of the DENIS assay showed robust diagnostic performance, even though the patients presented significant visual differences in the colour and consistency of the serum.

Rapid detection of sepsis biomarkers: Rapid turnaround time is an essential characteristic of a sepsis diagnostic device, as sepsis is a time-dependent emergency with a severe disease progression within hours. The diagnostic use of DENIS with minimal time-to-result enabled by time-resolved measurements is shown. The system can record real-time video of the sensor, from which NP binding signals are extracted and analysed in real-time.

In FIG. 12, time resolved PCT detection signals are presented from sera of representative sepsis patients, SIRS patients, and healthy individuals. Each plot shows mean signal from three PCT sensing spots and its 95% confidence interval in the shaded area. To establish the background signal and its variation, averaged signal from three BSA blocked areas are plotted and the running time averaged 95% confidence interval is computed. It is considered a reliable detection when the PCT signal's 95% lower confidence interval exceeds the background's upper confidence interval. The PCT cut-off detection times for sepsis, SIRS and healthy groups was characterized and it is observed that sepsis is detected in less than 5 mins and SIRS in around 10 mins, while PCT signal from healthy individuals did not significantly exceed background over 2 hours. These results show that the diagnosis of sepsis and SIRS can be performed in under 15 minutes of total time-to-result, including sample mixing, injection and read-out, which is particularly important in intensive care units.

The detection principle and system 1 is not limited to proteins and can be extended to small peptides, DNA, or RNA, as long as a pair of complementary recognition elements is available.

Au-NHA sensor fabrication: Plasmonic gold nanohole arrays (Au-NHAs) were produced using wafer-scale low-cost deep-UV lithography (DUVL) process and ion beam etching. Fused silica wafers with 4 in. diameter were used as substrate. The wafers were cleaned with RCA solution (1:1:5 $H_2O_2$:$NH_4OH$:$H_2O$ by volume) for 15 minutes, rinsed with deionized water for 5 minutes, and dried under nitrogen stream. Next, the cleaned wafers were coated with 10 nm of titanium (Ti) and 120 nm of gold (Au) using Alliance-Concept EVA 760 electron-gun evaporator. The NHAs with 200 nm diameter and 600 nm period were patterned over whole wafers using a 248 nm deep-UV stepper (ASML PAS 5500/300 DUV). The exposed wafers were treated with ion-beam etching (Oxford Instruments Plasma Lab 300 IBE), to transfer the nanohole arrays into metal films. The photoresist was stripped using oxygen plasma.

To label the Au-NHA sensors, QR codes were formed with 50 nm Ti film. The NHA wafers were coated with 1.3 μm thick lift-off positive photoresist (AZ1512) using Suss ACS200 Gen3 coater, and the QR microarray patterns were exposed using Heidelberg Instruments MLA150 Maskless Aligner. The resist was developed, and 50 nm Ti film was evaporated using an electron gun evaporator. Wafers covered with photoresists and Ti were diced into 1×1 $cm^2$ sensor chips, and the photoresist was removed from chips by immersing in resist remover with sonication at 70° C. overnight. The final chip cleaning was performed with oxygen plasma for 5 min at 500 W and 1 min immersion in RCA solution (1:1:5 $H_2O_2$:$NH_4OH$:$H_2O$) to ensure uniformly clean Au surface.

Chemicals and Biologicals: Ammonium hydroxide solution (ACS reagent, 28-30%), hydrogen peroxide ($H_2O_2$ 30%), bovine serum albumin (BSA) lyophilized, phosphate buffered saline (PBS), Tween20, and D-(+)-Trehalose dihydrate were purchased from Sigma-Aldrich. MCP-2F (co-poly-DMA-MAPS-NAS-fluorinated) polymer was bought from Lucidant. Ethanol (EtOH) absolute was from Thermo Chemicals. Pierce protease inhibitor (PI) tablets, recombinant human PCT and anti-PCT monoclonal antibodies QNO5 and CALC, used for spotting on Au-NHA and NP conjugation, respectively, were provided by ThermoFisher (BRAHMS). Anti human C-reactive protein (anti-CRP) monoclonal IgG antibodies PCR-196 and PCR-183, used as capture and recognition antibodies, respectively, were provided by Diesse Diagnostica Senese. Au-NP conjugation kit with lyophylised spherical Au-NPs of 100 nm dimeter coated with PEG (10 kDa) and activated with EDC-NHS, were purchased from Cytodiagnostics.

Au-NHA functionalization: Au-NHA chips were coated with MCP-2F (copoly-DMA-MAPS-NAS-fluorinated) polymer (Lucidant) to yield stable and reproducible functionalization with Ab microarray spots and prevent the sensors from non-specific fouling by serum and NPs. The MCP-2F polymer stock was diluted with coating solution from Lucidant, and the Au-NHA chips were immersed in the solution for 30 min at room temperature. Next, the Au-NHA sensors were washed in large volumes of mQ water and dried under nitrogen stream. The sensors were placed in a vacuum oven at 80° C. for 15 min (<2 mm Hg) to dry the polymer and ensure stable adhesion to the Au surface. Polymer-functionalized chips were immediately spotted with Ab microarrays, because EDC-NHS groups of the polymer degrade in the presence of air humidity.

The Ab microarrays were formed on the sensors by spotting Ab solutions on polymer coated Au-NHA surface using non-contact piezoelectric ultra-low volume dispensing system (sciFLEXARRAYER S3, Scienion). Spotting solutions containing Ab specific against PCT, or CRP, or mouse isotype control IgG, all at 200 μg/ml were prepared in PBS 1× with Trehalose (0.5% w/v) and Tween20 (0.01% w/v), to ensure uniform Ab distribution over each spot and stabilize Abs during sensor storage. Microarray spots of 400 pl were dispensed with a period of 400 μm inside a humid chamber. The humidity control was set at dew point (65% relative humidity) to prevent evaporation. The sensor chips with IgG microarrays were blocked with BSA (1% w/v) to inactivate non-reacted EDC-NHS groups and minimize the non-specific binding. The sensor chips were stored until use at 4° C. for up to 4 weeks. Au-NP functionalization: Au-NPs of 100 nm diameter coated with 10 kDa PEG and activated with EDC-NHS were functionalized with aPCT or aCRP antibodies according to the following protocol. Antibodies were diluted in protein re-suspension buffer (Cytodiagnostics) to 500 μg/ml concentration. The antibody solution (40 μl) was mixed with reaction buffer (50 μl, Cytodiagnostics), and added to the vial of lyophilized Au-NPs. The Au-NP mixture with Abs was incubated at room temperature for 4 hours with a mild mixing using Eppendorf ThermoMixer at 700 rpm. After incubation, 10 μl of quencher solution (Cytodiagnostics) was added to stop the reaction. The Au-NPs suspension was centrifuged at 150 rcf for 30 min to wash the NPs from non-reacted Abs. The supernatant was removed and NPs were resuspended in 1 ml of PBS 1× with 1% w/v BSA and 0.05% w/v Tween20. Centrifugation and resuspension steps were repeated 3 times. At the final resuspension step, Au-NPs pellet was diluted in a 100 μl of PBS 1× with 1% w/v BSA and 0.05% w/v Tween20 to obtain Au-NP stock solution with optical density OD=20, or 7.7E+10 NP/ml. The Ab-NPs solution was stored at 4° C. for up to 4 weeks. Before performing bioassay, Ab-NPs were vortexed at 800 rpm for 30 seconds to resuspend the NPs. Biobank samples: Samples and data from representative patients selected for this study were provided by the Sepsis Bank of Vall d'Hebron University Hospital Biobank (PT17/0015/0047), integrated in the Spanish National Biobanks Network, and they were processed following standard operating procedures with the appropriate approval of the Clinical Research Ethics Committee (approval reference number PR(AG)11/2016). The serum samples were stored in 500 μl aliquots at −80° C. in cryovials and thawed on ice on the day of measurement. Samples were handled on ice and protected from light.

Serum bioassays: The bioassays were performed by mixing patient serum with the Ab-NP conjugates (anti-PCT or anti-CRP) and a stabilizing buffer and injecting the mixture into the sensor measurement chamber. A 20 μl aliquot of serum sample was mixed with 16 μl of buffer and 4 μl of anti-PCT Ab-NP stock by gentle pipetting and inserted onto the measurement chamber. In the case of CRP measurements, the patient serum was first diluted 50'000 times in PBS 1 × with bovine serum albumin 7%. Then a 20 μl aliquot of the diluted serum was mixed with 16 μl of measurement buffer and 4 μl of anti-CRP Ab-NPs by gentle pipetting and inserted to the sensor chamber. Sensor chamber was formed by placing a capillarity-based disposable microfluidic cartridge (Microtec) on the Au-NHA sensor chip using a silicone spacer for sealing. The loaded sensor was either immediately inserted into the portable reader for real-time measurements or incubated at room temperature, and end-point read-outs were taken at the end of the incubation period (2 hours).

The stabilizing buffer was optimized to ensure optimal bioassay performance and prevent NPs aggregation during the measurements. The buffer consists of 0.05% PBST 1× and 50 mM NaOH mixed in 3:1 volume ratio.

Calibration measurements: In order to perform calibration measurements of the PCT bioassay, known concentrations of recombinant human PCT (50 pg/ml, 100 pg/ml, 300 pg/ml, 500 pg/ml, 1 ng/ml, 3 ng/ml, 10 ng/ml, and 50 ng/ml) were spiked in 7% BSA PBS 1× with protease inhibitors (1 tablet per 50 ml of buffer). Next, the calibration samples, as well as a blank negative control containing BSA 7% in PBS 1× and PI without PCT, were measured identically to the serum bioassays. A 20 µl aliquot of calibration sample was mixed with 16 µl of measurement buffer and 4 µl of Ab-NP, incubated over 2 hours and measured with the portable reader to obtain the corresponding signals. For each calibration sample, at least five different antibody sensing spots were measured to compute the mean and the standard deviation of the signal.

To obtain calibration curve for CRP, we used serial dilutions of a real human sample with a known CRP concentration characterized by an immunoturbidimetric test (267 µg/ml). The sample was diluted in BSA 7% PBS 1× and the measurements were performed identically to PCT. Calibration curves for PCT and CRP were fitted to the measured points, according to the following equation:

$$y = d + \frac{a-d}{1+\left(\frac{x}{c}\right)^b}$$

Where a is a theoretical response at zero concentration, b is a slope factor, c is a concentration inflection point, and d is a theoretical response at saturation.

Optical reader: The nanoplasmonic imager 1 is made of off-the-shelf optical components and effectively comprises a portable bright-field imaging microscope. A narrowband light emitting diode (LED) source (Thorlabs M660L4) in combination with a bandpass filter with 660 nm center wavelength and 10 nm full-width-at-half-maximum (Thorlabs) is used for narrow-band illumination. The light from the LED is collimated with an aspherical condenser lens (Thorlabs). A custom Al holder for the sensor chamber was fabricated to accomodate the sensor inside the reader. The light is transmitted through the sample chamber, modulated by Au-NHA sensor, and the imaging is performed using a 50× objective (Nikon) and a black-and-white CMOS camera (IDS B-UI-3200SE-M-GL). The CMOS camera has 4104×3006 pixels with 3.45 µm pixel size. The system enables imaging of ~900 µm×700 µm field-of-view (FOV) area with an about 1.5 µm resolution (diffraction-limited spot). The reader dimensions are 10×10×35 cm and the weight is less than 1 kg.

Image processing: Image acquisition and processing was performed using custom Matlab functions and a graphical user interface from a laptop connected to the CMOS camera. Images from Au-NHA sensors were recorder using custom auto-exposure function to ensure similar intensity profiles across all images, and so that image histogram is always covered by the dynamic range of the CMOS. The images were normalized by the background illumination to exclude the source variations. To extract the NP signal, image areas were analyzed using a fixed intensity threshold to quantify bound NPs. The percentage number of pixels in an area darker than the threshold was used for quantification. The intensity threshold was optimized by matching plasmonic images to scanning electron micrographs of identical Au-NHA areas to maximize the number of detected NPs, while minimizing false-positive signals. Importantly, Au-NP aggregates can be identified and filtered out from the signal, as described previously. A custom Matlab function was used to recognize QR codes from the images and extract encoded information. For the end-point measurements at least five different FOV were acquired and analyzed from each sensor chip for statistical significance. In order to control for non-specific NPs binding and background fluctuations, signal from each measured spot was corrected by subtracting the signal from adjacent BSA blocked background area. During time-resolved measurements, the images of a single FOV were recorded with 30 seconds interval. Each field of view had at least three antibody spots, which enabled to assess the mean and standard deviation of the signal from each frame. In order to evaluate detection cut-off times signal from three PCT sensing spots and its 95% confidence interval (±1.96*δ) were estimated at each time point. To establish the background signal and its variation, we plot average from three BSA blocked areas at each time point and compute running time averaged 95% confidence interval. The time averaged standard deviation at every time point T was computed to incorporate variances of background signals of all individual previous frames $t_i$:

$$\delta_T = \sqrt{\frac{\sum_{i=0}^{n} \delta_{t_i}^2}{n}}$$

A reliable detection was considered to be when the PCT signal's 95% lower confidence interval exceeds the background's upper confidence interval.

REFERENCES INCORPORATED HEREIN BY REFERENCE (1) Fan, X.; White, I. M.; Shopova, S. I.; Zhu, H.; Suter, J. D.; Sun, Y. Sensitive Optical Biosensors for Unlabeled Targets: A Review. *Anal. Chim. Acta* 2008, 620 (1), 8-26.

(2) Anker, J. N.; Hall, W. P.; Lyandres, O.; Shah, N. C.; Zhao, J.; Van Duyne, R. P. Biosensing with Plasmonic Nanosensors. In *Nanoscience And Technology: A Collection of Reviews from Nature Journals*; World Scientific, 2010; pp 308-319.

(3) Zeng, S.; Baillargeat, D.; Ho, H.-P.; Yong, K.-T. Nanomaterials Enhanced Surface Plasmon Resonance for Biological and Chemical Sensing Applications. *Chem. Soc. Rev.* 2014, 43 (10), 3426-3452.

(4) Lopez, G. A.; Estevez, M.-C.; Soler, M.; Lechuga, L. M. Recent Advances in Nanoplasmonic Biosensors: Applications and Lab-on-a-Chip Integration. *Nanophotonics* 2017, 6 (1), 123-136.

(5) Di Fabrizio, E.; Schlücker, S.; Wenger, J.; Regmi, R.; Rigneault, H.; Calafiore, G.; West, M.; Cabrini, S.; Fleischer, M.; Van Hulst, N. F. Roadmap on Biosensing and Photonics with Advanced Nano-Optical Methods. *J. Opt.* 2016, 18 (6), 063003.

(6) Dantham, V. R.; Holler, S.; Kolchenko, V.; Wan, Z.; Arnold, S. Taking Whispering Gallery-Mode Single Virus Detection and Sizing to the Limit. *Appl. Phys. Lett.* 2012, 101 (4), 043704.

(7) Kosaka, P. M.; Pini, V.; Ruz, J. J.; González, M. U.; Ramos, D.; Calleja, M.; Tamayo, J.; da Silva, R. A. Detection of Cancer Biomarkers in Serum Using a Hybrid Mechanical and Optoplasmonic Nanosensor. *Nat. Nanotechnol.* 2014, 9 (12).

(8) Rissin, D. M.; Kan, C. W.; Campbell, T. G.; Howes, S. C.; Fournier, D. R.; Song, L.; Piech, T.; Patel, P. P.; Chang, L.; Rivnak, A. J. Single-Molecule Enzyme-Linked Immunosorbent Assay Detects Serum Proteins at Subfemtomolar Concentrations. *Nat. Biotechnol.* 2010, 28 (6), 595-599.

(9) Dickson, R. M.; Cubitt, A. B.; Tsien, R. Y.; Moerner, W. E. On/off Blinking and Switching Behaviour of Single Molecules of Green Fluorescent Protein. *Nature* 1997, 388 (6640), 355-358.

(10) Jain, A.; Liu, R.; Ramani, B.; Arauz, E.; Ishitsuka, Y.; Ragunathan, K.; Park, J.; Chen, J.; Xiang, Y. K.; Ha, T. Probing Cellular Protein Complexes Using Single-Molecule Pull-Down. *Nature* 2011, 473 (7348), 484-488.

(11) Bozhevolnyi, S. I.; Volkov, V. S.; Devaux, E.; Laluet, J.-Y.; Ebbesen, T. W. Channel Plasmon Subwavelength Waveguide Components Including Interferometers and Ring Resonators. *Nature* 2006, 440 (7083), 508-511.

(12) Su, J.; Goldberg, A. F.; Stoltz, B. M. Label-Free Detection of Single Nanoparticles and Biological Molecules Using Microtoroid Optical Resonators. *Light Sci. Appl.* 2016, 5 (1), e16001.

(13) Baaske, M. D.; Foreman, M. R.; Vollmer, F. Single-Molecule Nucleic Acid Interactions Monitored on a Label-Free Microcavity Biosensor Platform. *Nat. Nanotechnol.* 2014, 9 (11), 933-939.

(14) Sreekanth, K. V.; Alapan, Y.; ElKabbash, M.; Ilker, E.; Hinczewski, M.; Gurkan, U. A.; De Luca, A.; Strangi, G. Extreme Sensitivity Biosensing Platform Based on Hyperbolic Metamaterials. *Nat. Mater.* 2016, 15 (6), 621.

(15) Walt, D. R. *Optical Methods for Single Molecule Detection and Analysis*; ACS Publications, 2012.

(16) Raether, H. Surface Plasmons on Smooth Surfaces. In *Surface plasmons on smooth and rough surfaces and on gratings*; Springer, 1988; pp 4-39.

(17) Shen, Y.; Zhou, J.; Liu, T.; Tao, Y.; Jiang, R.; Liu, M.; Xiao, G.; Zhu, J.; Zhou, Z.-K.; Wang, X. Plasmonic Gold Mushroom Arrays with Refractive Index Sensing Figures of Merit Approaching the Theoretical Limit. *Nat. Commun.* 2013, 4, 2381.

(18) Zijlstra, P.; Paulo, P. M.; Orrit, M. Optical Detection of Single Non-Absorbing Molecules Using the Surface Plasmon Resonance of a Gold Nanorod. *Nat. Nanotechnol.* 2012, 7 (6), 379-382.

(19) Lindquist, N. C.; Nagpal, P.; McPeak, K. M.; Norris, D. J.; Oh, S.-H. Engineering Metallic Nanostructures for Plasmonics and Nanophotonics. *Rep. Prog. Phys.* 2012, 75 (3), 036501.

(20) Kabashin, A. V.; Evans, P.; Pastkovsky, S.; Hendren, W.; Wurtz, G. A.; Atkinson, R.; Pollard, R.; Podolskiy, V. A.; Zayats, A. V. Plasmonic Nanorod Metamaterials for Biosensing. *Nat. Mater.* 2009, 8 (11), 867-871.

(21) Homola, J. Surface Plasmon Resonance Sensors for Detection of Chemical and Biological Species. *Chem. Rev.* 2008, 108 (2), 462-493.

(22) Mazzotta, F.; Johnson, T. W.; Dahlin, A. B.; Shaver, J.; Oh, S.-H.; Höök, F. Influence of the Evanescent Field Decay Length on the Sensitivity of Plasmonic Nanodisks and Nanoholes. *Acs Photonics* 2015, 2 (2), 256-262.

(23) Unser, S.; Bruzas, I.; He, J.; Sagle, L. Localized Surface Plasmon Resonance Biosensing: Current Challenges and Approaches. *Sensors* 2015, 15 (7), 15684-15716.

(24) Coskun, A. F.; Cetin, A. E.; Galarreta, B. C.; Alvarez, D. A.; Altug, H.; Ozcan, A. Lensfree Optofluidic Plasmonic Sensor for Real-Time and Label-Free Monitoring of Molecular Binding Events over a Wide Field-of-View. *Sci. Rep.* 2014, 4, 6789. https://doi.org/10.1038/srep06789.

(25) Cetin, A. E.; Coskun, A. F.; Galarreta, B. C.; Huang, M.; Herman, D.; Ozcan, A.; Altug, H. Handheld High-Throughput Plasmonic Biosensor Using Computational on-Chip Imaging. *Light Sci. Appl.* 2014, 3 (1), e122.

(26) Ballard, Z. S.; Shir, D.; Bhardwaj, A.; Bazargan, S.; Sathianathan, S.; Ozcan, A. Computational Sensing Using Low-Cost and Mobile Plasmonic Readers Designed by Machine Learning. *ACS Nano* 2017, 11 (2), 2266-2274.

(27) Najiminaini, M.; Vasefi, F.; Kaminska, B.; Carson, J. J. Nanohole-Array-Based Device for 2D Snapshot Multispectral Imaging. *Sci. Rep.* 2013, 3.

(28) Ebbesen, T. W.; Lezec, H. J.; Ghaemi, H. F.; Thio, T.; Wolff, P. A. Extraordinary Optical Transmission through Sub-Wavelength Hole Arrays. *Nature* 1998, 391 (6668), 667-669.

(29) Couture, M.; Ray, K. K.; Poirier-Richard, H.-P.; Crofton, A.; Masson, J.-F. 96-Well Plasmonic Sensing with Nanohole Arrays. *ACS Sens.* 2016, 1 (3), 287-294. https://doi.org/10.1021/acssensors.5b00280.

(30) Sharpe, J. C.; Mitchell, J. S.; Lin, L.; Sedoglavich, N.; Blaikie, R. J. Gold Nanohole Array Substrates as Immunobiosensors. *Anal. Chem.* 2008, 80 (6), 2244-2249.

(31) Im, H.; Shao, H.; Park, Y. I.; Peterson, V. M.; Castro, C. M.; Weissleder, R.; Lee, H. Label-Free Detection and Molecular Profiling of Exosomes with a Nano-Plasmonic Sensor. *Nat. Biotechnol.* 2014, 32 (5), 490-495.

(32) Yanik, A. A.; Huang, M.; Kamohara, 0.; Artar, A.; Geisbert, T. W.; Connor, J. H.; Altug, H. An Optofluidic Nanoplasmonic Biosensor for Direct Detection of Live Viruses from Biological Media. *Nano Lett.* 2010, 10 (12), 4962-4969.

(33) Jackman, J. A.; Linardy, E.; Yoo, D.; Seo, J.; Ng, W. B.; Klemme, D. J.; Wittenberg, N. J.; Oh, S.-H.; Cho, N.-J. Plasmonic Nanohole Sensor for Capturing Single Virus-Like Particles toward Virucidal Drug Evaluation. *Small* 2016, 12 (9), 1159-1166.

(34) Soler, M.; Belushkin, A.; Cavallini, A.; Kebbi-Beghdadi, C.; Greub, G.; Altug, H. Multiplexed Nanoplasmonic Biosensor for One-Step Simultaneous Detection of Chlamydia Trachomatis and Neisseria Gonorrhoeae in Urine. *Biosens. Bioelectron.* 2017, 94, 560-567.

(35) Li, X.; Soler, M.; Özdemir, C. I.; Belushkin, A.; Yesilkoy, F.; Altug, H. Plasmonic Nanohole Array Biosensor for Label-Free and Real-Time Analysis of Live Cell Secretion. *Lab. Chip* 2017.

(36) Black, S.; Kushner, I.; Samols, D. C-Reactive Protein. *J. Biol. Chem.* 2004, 279 (47), 48487-48490.

(37) Pradhan, A. D.; Manson, J. E.; Rifai, N.; Buring, J. E.; Ridker, P. M. C-Reactive Protein, Interleukin 6, and Risk of Developing Type 2 Diabetes Mellitus. *Jama* 2001, 286 (3), 327-334.

(38) Simon, L.; Gauvin, F.; Amre, D. K.; Saint-Louis, P.; Lacroix, J. Serum Procalcitonin and C-Reactive Protein Levels as Markers of Bacterial Infection: A Systematic Review and Meta-Analysis. *Clin. Infect. Dis.* 2004, 39 (2), 206-217.

(39) Ridker, P. M.; Danielson, E.; Fonseca, F. A.; Genest, J.; Gotto Jr, A. M.; Kastelein, J. J.; Koenig, W.; Libby, P.; Lorenzatti, A. J.; MacFadyen, J. G. Rosuvastatin to Prevent Vascular Events in Men and Women with Elevated C-Reactive Protein. *N. Engl. J. Med.* 2008, 359 (21), 2195.

(40) Ridker, P. M.; Cannon, C. P.; Morrow, D.; Rifai, N.; Rose, L. M.; McCabe, C. H.; Pfeffer, M. A.; Braunwald, E. C-Reactive Protein Levels and Outcomes after Statin Therapy. *N. Engl. J. Med.* 2005, 352 (1), 20-28.

(41) Harris, T. B.; Ferrucci, L.; Tracy, R. P.; Corti, M. C.; Wacholder, S.; Ettinger, W. H.; Heimovitz, H.; Cohen, H. J.; Wallace, R. Associations of Elevated Interleukin-6 and C-Reactive Protein Levels with Mortality in the Elderly. *Am. J. Med.* 1999, 106 (5), 506-512.

(42) Niu, R.; Liu, Y.; Zhang, Y.; Zhang, Y.; Wang, H.; Wang, Y.; Wang, W.; Li, X. ITRAQ-Based Proteomics Reveals Novel Biomarkers for Idiopathic Pulmonary Fibrosis. *PloS One* 2017, 12 (1), e0170741.

(43) F Yesilkoy; R Terborg; J Pello; A Belushkin; Y Jahani; V Pruneri; H Altug. Phase-Sensitive Plasmonic Biosensor Using a Portable and Large Field of View Interferometric Microarray Imager. *Light Sci. Appl.* 2018. https://doi.org/doi: 10.1038.

(44) Wood, R. W. On a Remarkable Case of Uneven Distribution of Light in a Diffraction Grating Spectrum (from Philosophical Magazine 1902). *SPIE Milest. Ser. MS* 1993, 83, 287-287.

(45) Brolo, A. G.; Gordon, R.; Leathem, B.; Kavanagh, K. L. Surface Plasmon Sensor Based on the Enhanced Light Transmission through Arrays of Nanoholes in Gold Films. *Langmuir* 2004, 20 (12), 4813-4815.

(46) Bergeret, G.; Gallezot, P. Particle Size and Dispersion Measurements. *Handb. Heterog. Catal. Online* 2008, 738-765.

(47) Zheng, T.; Bott, S.; Huo, Q. Techniques for Accurate Sizing of Gold Nanoparticles Using Dynamic Light Scattering with Particular Application to Chemical and Biological Sensing Based on Aggregate Formation. *ACS Appl. Mater. Interfaces* 2016, 8 (33), 21585-21594. https://doi.org/10.1021/acsami.6b06903.

(48) Nanoparticle Size, Zeta Potential, and Molecular Weight Analyzer SZ-100 HORIBA Scientific-HORIBA http://www.horiba.com/scientific/products/particle-characterization/particle-size-analysis/details/sz-100-7245/?referrer=AZONANO (accessed Mar. 21, 2019).

(49) Dellinger, R. P.; Levy, M. M.; Rhodes, A.; Annane, D.; Gerlach, H.; Opal, S. M.; Sevransky, J. E.; Sprung, C. L.; Douglas, I. S.; Jaeschke, R. Surviving Sepsis Campaign: International Guidelines for Management of Severe Sepsis and Septic Shock, 2012. *Intensive Care Med.* 2013, 39 (2), 165-228.

(50) Cetin, A. E.; Etezadi, D.; Galarreta, B. C.; Busson, M. P.; Eksioglu, Y.; Altug, H. Plasmonic Nanohole Arrays on a Robust Hybrid Substrate for Highly Sensitive Label-Free Biosensing. *ACS Photonics* 2015, 2 (8), 1167-1174.

The entire contents of each of the above references are herewith incorporated by reference.

The invention claimed is:

1. Plasmonic biosensor system including:
a nano-hole array device comprising at least one nano-hole array including a plurality of nano holes, the at least one nano-hole array is functionalized by at least one molecule attached to the at least one nano-hole array to bind to a target antigen or biomarker,
an image sensor for capturing light provided by a light source for illuminating the at least one nano-hole array and transmitted through the at least one nano-hole array, and
at least one or a plurality of nano-particles configured to be received by the nano-holes of the at least one nano-hole array, the at least one or the plurality of nano-particles comprising at least one metal and the at least one or the plurality of nano-particles are functionalized by at least one further molecule attached to the at least one or each nano-particle, the at least one further molecule configured to bind or conjugate to a target antigen or biomarker,
wherein the nano-holes are configured to produce an extraordinary optical transmission resonance; and
wherein the system further includes a processor configured to receive image data from the image sensor and configured to determine or count, from the received image data, the nano-holes on the at least one nano-hole array having received a single nano-particle at which a quenching of transmission intensity of an extraordinary optical transmission occurs.

2. System according to claim 1, wherein the at least one nano-hole array is configured to generate surface plasmons.

3. System according to claim 1, wherein the system further includes a memory configured to store or storing processor executable instructions, the processor being configured to execute the processor executable instructions, the processor executable instructions comprising instructions to determine or count the nano-holes on the at least one nano-hole array at which quenching of transmission intensity occurs using the received image data.

4. System according to claim 3, wherein the processor is configured to generate data or an image map identifying nano-holes on the at least one nano-hole array at which quenching of transmission intensity occurs and/or the processor executable instructions comprise instructions to generate data or an image map identifying nano-holes on the at least one nano-hole array at which quenching of transmission intensity occurs.

5. System according claim 4, wherein the data or the image map is configured to provide a representation of at least one nano-particle in at least one nano-hole or in proximity of the nano-hole (NH) on the at least one nano-hole array.

6. System according to claim 3, wherein the quenching of transmission intensity corresponds to the presence of a nano-particle in a nano-hole or in proximity of the nano-hole and the detection of a target antigen or target biomarker.

7. System according to claim 3, wherein the processor is configured to generate data or an image map by subtracting intensity values of at least a part of a first image acquired in the absence of nano-particles on the at least one nano-hole array from intensity values of at least a part of a second image acquired in the presence of nano-particles on the at least one nano-hole array, and/or the processor executable instructions comprise instructions to generate data or an image map by subtracting intensity values of at least a part of a first image acquired in the absence of nano-particles on the at least one nano-hole array from intensity values of at least a part of a second image acquired in the presence of nano-particles on the at least one nano-hole array.

8. System according to claim 7, wherein the processor is configured to align the first image with the second image using at least one alignment mark present in the first and second images, and/or the processor executable instructions comprise instructions to align the first image with the second image using at least one alignment mark present in the first and second images.

9. System according to claim 1, wherein the at least one or the plurality of nano-particles has an average diameter that is between 25% and 100% of the average diameter of the nano-hole at an external surface of the at least one nano-hole array.

10. System according to claim 1, wherein the at least one or the plurality of nano-particles are sub-wavelength in size.

11. System according to claim 1, wherein the nano-holes are configured as a periodic nano-hole array or arranged in a periodic array arrangement.

12. System according to claim 1, wherein the nano-holes of the nano-hole array have a symmetric geometry.

13. System according to claim 1, wherein the at least one nano-hole array includes at least one or a plurality of alignment marks, and/or at least one or a plurality of quick response codes.

14. System according to claim 1, wherein the nano-holes are metallic nano-holes or noble metal nano-holes.

15. System according to claim 1, wherein the nano-particle is configured to be fully received through an aperture of the nano-hole of the at least one nano-hole array for entrapment inside the nano-hole.

16. Plasmonic bio-sensing method including the steps of:
providing a nano-hole array device comprising at least one nano-hole array including a plurality of nano holes,
providing a light source for illuminating the at least one nano-hole array,
providing an image sensor for capturing light provided by the light source and transmitted through the at least one nano-hole array, and
providing at least one or a plurality of nano-particles configured to be received by the nano-holes of the at least one nano-hole array, the at least one or the plurality of nano-particles comprising or consisting solely of at least one metal; and
functionalizing the at least one nano-hole array to capture a target antigen or biomarker, by attaching at least one molecule to the at least one nano-hole array, the at least one molecule being configured to bind to a target antigen or biomarker; and
functionalizing the at least one or the plurality of nano-particles with at least one molecule configured to bind or conjugate to the target antigen or biomarker by attaching at least one further molecule to the at least one or each nano-particle, the at least one further molecule being configured to bind or conjugate to a target antigen or biomarker;
wherein the nano-holes are configured to produce an extraordinary optical transmission resonance, and
wherein the method further includes the step of determining or counting, from received image data, the nano-holes on the at least one nano-hole array having received a single nano-particle and at which a quenching of transmission intensity of an extraordinary optical transmission resonance occurs.

* * * * *